(12) United States Patent
Spier et al.

(10) Patent No.: US 9,523,121 B2
(45) Date of Patent: Dec. 20, 2016

(54) METHODS AND COMPOSITIONS FOR PCR USING BLOCKED AND UNIVERSAL PRIMERS

(71) Applicant: UniTaq Bio, Los Altos, CA (US)

(72) Inventors: Eugene Spier, Los Altos, CA (US); Karl Guegler, Menlo Park, CA (US)

(73) Assignee: Uni Taq Bio, Los Altos, CA (US)

( * ) Notice: Subject to any disclaimer, the term of this patent is extended or adjusted under 35 U.S.C. 154(b) by 16 days.

(21) Appl. No.: 14/154,117

(22) Filed: Jan. 13, 2014

(65) Prior Publication Data

US 2014/0329245 A1    Nov. 6, 2014

Related U.S. Application Data

(60) Provisional application No. 61/751,869, filed on Jan. 13, 2013.

(51) Int. Cl.
*C12P 19/34* (2006.01)
*C12Q 1/68* (2006.01)

(52) U.S. Cl.
CPC ..................... *C12Q 1/686* (2013.01)

(58) Field of Classification Search
USPC .............................. 435/6.12, 91.2
See application file for complete search history.

(56) References Cited

U.S. PATENT DOCUMENTS

| | | | |
|---|---|---|---|
| 5,792,607 A | 8/1998 | Backman et al. | |
| 6,027,889 A * | 2/2000 | Barany ................ | C12Q 1/6813 435/6.12 |
| 8,481,292 B2 | 7/2013 | Casbon et al. | |
| 2004/0067559 A1* | 4/2004 | McCarthy ............. | C12Q 1/682 435/91.2 |
| 2009/0148838 A1 | 6/2009 | Loehrlein et al. | |
| 2009/0325169 A1 | 12/2009 | Walder et al. | |
| 2010/0233699 A1 | 9/2010 | Nazarenko et al. | |
| 2011/0092387 A1 | 4/2011 | Monforte et al. | |
| 2013/0224743 A1 | 8/2013 | Casbon et al. | |

FOREIGN PATENT DOCUMENTS

| | | |
|---|---|---|
| WO | WO 2005/098042 A2 | 10/2005 |
| WO | WO 2010/017932 A1 | 2/2010 |
| WO | WO 2010/115154 A1 | 10/2010 |
| WO | WO 2012/135053 A2 | 4/2012 |

OTHER PUBLICATIONS

International Search Report dated May 29, 2014 for related application PCTUS2014011343.

(Continued)

*Primary Examiner* — Kenneth Horlick

(74) *Attorney, Agent, or Firm* — Quinc Intellectual Property Law Group P.C.; Gary Baker

(57) ABSTRACT

Provided herein are methods and compositions for performing PCR with primers with blocked 3'-ends that are unblocked when these primers anneal to the template. The multiplexed PCR can be used as real-time qPCR, for end-point detection or as enrichment method for next generation sequencing (NGS). Also described herein are methods and compositions to improve sensitivity of mutation-specific PCR when targeting closely-spaced mutations.

20 Claims, 11 Drawing Sheets

(56) References Cited

OTHER PUBLICATIONS

Bi and Stambrook (1998) "Detection of known mutation by proofreading PCR." *Nucleic Acids Res.*, 26(12):3073-3075.
Clementi, et al. (1993) "Quantitative PCR and RT-PCR in virology." *PCR Methods Appl.*, 2:191-196.
Didenko, V.V. (2001) "DNA probes using fluorescence resonance energy transfer (FRET): designs and applications." *BioTechniques*, 31:1106-1121.
Diviacco, et al. (1992) "A novel procedure for quantitative polymerase chain reaction by coamplification of competitive templates." Gene, 122:313-20.
Dobosy, et al., (2011) "RNase H-dependent PCR (rhPCR): improved specificity and single nucleotide polymorphism detection using blocked cleavable primers." *BMC Biotechnology*, 11:80.
Freeman, et al. (1999) "Quantitative RT-PCR: pitfalls and potential." *BioTechniques*, 26:112-125.
Gu, et al (2003) "Multiplexed, real-time PCR for quantitative detection of human adenovirus." *J. Clin. Microbiol.*, 41:4636-4641.
Kutyavin, et al. (2006) "A novel endonuclease IV post-PCR genotyping system." *Nucleic Acids Res.*, 34(19):e128.
Lin-Ling, et al. (2005) "Single-base discrimination mediated by proofreading inert allele specific primers." *J. Biochem. Mol. Biol.*, 38(1):24-27.
Longo, et al. (1990) "Use of uracil DNA glycosylase to control carry-over contamination in polymerase chain reactions." *Gene*, 93:125-128.
Lutfalla, G. and Uze, G. (2006) "Performing quantitative reverse-transcribed polymerase chain reaction experiments." *Methods Enzymol.*, 410:386- 400.
MacKay, et al (2002) "Real-time PCR in virology." *Nucleic Acids Res.*, 30: 1292-1305.
MacKay, J. and Landt, O. (2007) "Real-time PCR fluorescent chemistries." *Methods Mol. Biol.*, 353:237-262.
Nguyen-Dumont, et. al (2013) "A high-plex PCR approach for massively parallel sequencing." *BioTechniques*, 55:69-74.
Wen, et al. (2012) "Universal Multiplex PCR: a novel method of simultaneous amplification of multiple DNA fragments." *Plant Methods*, 8(I):32.

\* cited by examiner

SEQUENCE LISTING

```
<160> NUMBER OF SEQ ID NOS: 13

<210> SEQ ID NO 1
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 1
tgtgccgaac gtgtaccaat ccaatatgcc aggtgccatg gtgcttccgg cggtac        56

<210> SEQ ID NO 2
<211> LENGTH: 72
<212> TYPE: DNA
<213> ORGANISM: Artificial Sequence
```

```
<220> FEATURE:
<223> OTHER INFORMATION: synthetic oligonucleotide primer
<220> FEATURE:
<221> NAME/KEY: misc_feature
<222> LOCATION: (58)..(58)
<223> OTHER INFORMATION: N is dSpacer (abasic site mimic)
<220> FEATURE:
<221> NAME/KEY: misc_feature
<222> LOCATION: (72)..(72)
<223> OTHER INFORMATION: N is C3 spacer (abasic site mimic)

<400> SEQUENCE: 2
tgtgccgaac gtgtaccaat ccaatatgcc aggtgccatg gcttgcagct cctggtgntt      60
ccggcggtac an                                                          72

<210> SEQ ID NO 3
<211> LENGTH: 73
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (57)..(57)
<223> OTHER INFORMATION: N is C3 spacer (abasic site mimic)
<220> FEATURE:
<221> NAME/KEY: misc_feature
<222> LOCATION: (73)..(73)
<223> OTHER INFORMATION: N is C3 spacer (abasic site mimic)

<400> SEQUENCE: 3
tgtgccgaac gtgtaccaat ccaatatgcc aggtgccatg gtgcttccgg cggtacnctt      60
taggtccttt ccn                                                         73

<210> SEQ ID NO 4
<211> LENGTH: 45
<212> TYPE: DNA
<213> ORGANISM: Artificial Sequence
<220> FEATURE:
<223> OTHER INFORMATION: synthetic oligonucleotide primer

<400> SEQUENCE: 4
ttgtctctgc gacccatcaa gtggagtcat gcttatatgg agcaa                      45

<210> SEQ ID NO 5
<211> LENGTH: 39
<212> TYPE: DNA
<213> ORGANISM: Artificial Sequence
<220> FEATURE:
<223> OTHER INFORMATION: synthetic oligonucleotide primer

<400> SEQUENCE: 5
tccaatatgc caggtgccat tgtctctgcg acccatcaa                             39

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 6
cgtgtgccga acgtgtacca at                                               22

<210> SEQ ID NO 7
<211> LENGTH: 101
<212> TYPE: DNA
```

<213> ORGANISM: Artificial Sequence
<220> FEATURE:
<223> OTHER INFORMATION: synthetic oligonucleotide template
<220> FEATURE:
<221> NAME/KEY: misc_feature
<222> LOCATION: (101)..(101)
<223> OTHER INFORMATION: N is C3 spacer (abasic site mimic)

<400> SEQUENCE: 7
gtggagtcat gcttatatgg agcaaaacta ctgtagagcc cacacctggg aaaggaccta    60
aagtgtaccg ccggaagcac caggagctgc aagccatgca n                       101

<210> SEQ ID NO 8
<211> LENGTH: 50
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (46)..(46)
<223> OTHER INFORMATION: N is ribo-G
<220> FEATURE:
<221> NAME/KEY: misc_feature
<222> LOCATION: (48)..(49)
<223> OTHER INFORMATION: N is C3 spacer (abasic site mimic)

<400> SEQUENCE: 8
caagctgatc cgtacaacgc tgacgtcccg ctgtcggggt tgaccnanna               50

<210> SEQ ID NO 9
<211> LENGTH: 49
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (44)..(44)
<223> OTHER INFORMATION: N is ribo-U
<220> FEATURE:
<221> NAME/KEY: misc_feature
<222> LOCATION: (49)..(49)
<223> OTHER INFORMATION: N is C3 spacer (abasic site mimic)

<400> SEQUENCE: 9
caagctgatc cgtacagtcg tgcacacgct gtcggggttg accnacaan                49

<210> SEQ ID NO 10
<211> LENGTH: 48
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (43)..(43)
<223> OTHER INFORMATION: N is ribo-U
<220> FEATURE:
<221> NAME/KEY: misc_feature
<222> LOCATION: (48)..(48)
<223> OTHER INFORMATION: N is C3 spacer (abasic site mimic)

<400> SEQUENCE: 10
caagctgatc cgtacagagg accatgctgt cggggttgac ccncaagn                 48

<210> SEQ ID NO 11
<211> LENGTH: 49
<212> TYPE: DNA
<213> ORGANISM: Artificial Sequence

```
<220> FEATURE:
<223> OTHER INFORMATION: synthetic oligonucleotide primer
<220> FEATURE:
<221> NAME/KEY: misc_feature
<222> LOCATION: (45)..(45)
<223> OTHER INFORMATION: N is ribo-A
<220> FEATURE:
<221> NAME/KEY: misc_feature
<222> LOCATION: (47)..(48)
<223> OTHER INFORMATION: N is C3 spacer (abasic site mimic)

<400> SEQUENCE: 11
caagctgatc cgtacagagc tgtagtccgc tgtcggggtt gaccnanna                      49

<210> SEQ ID NO 12
<211> LENGTH: 47
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (41)..(41)
<223> OTHER INFORMATION: N is ribo-A
<220> FEATURE:
<221> NAME/KEY: misc_feature
<222> LOCATION: (47)..(47)
<223> OTHER INFORMATION: N is C3 spacer (abasic site mimic)

<400> SEQUENCE: 12
caagctgatc cgtacatcca ataacgtgtc ggggttgacc ngcaaan                        47

<210> SEQ ID NO 13
<211> LENGTH: 49
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (45)..(45)
<223> OTHER INFORMATION: N is ribo-G
<220> FEATURE:
<221> NAME/KEY: misc_feature
<222> LOCATION: (47)..(48)
<223> OTHER INFORMATION: N is C3 spacer (abasic site mimic)

<400> SEQUENCE: 13
caagctgatc cgtacaacca cagtgtcgct gtcggggttg acccncnng                      49
```

METHODS AND COMPOSITIONS FOR PCR USING BLOCKED AND UNIVERSAL PRIMERS

CROSS-REFERENCE TO RELATED APPLICATION

This application is a non-provisional utility patent application claiming priority to and benefit of the following prior provisional patent application: U.S. Ser. No. 61/751,869 filed on Jan. 13, 2013, entitled "Methods and compositions for PCR using blocked and universal primers" by Eugene Spier. This provisional application is incorporated herein by reference in its entirety for all purposes.

BACKGROUND OF THE INVENTION

PCR-based nucleic acid detection typically employs two primers that anneal to opposite strands of a DNA target. PCR can be multiplexed to amplify several targets in a well or droplet. One of the challenges of PCR is that primers can prime non-specifically on themselves forming primer dimers or on DNA targets that are similar to intended targets. This non-specific priming can occur during single-plex PCR, but is markedly more likely in multiplex PCR. For example, 10-plex PCR requires 10 primer pairs (20 primers) that can form 19+18+ . . . 1=19*10=190 different pairs, each potentially causing a non-specific amplification product such as a primer dimer.

Various methods have been described for overcoming non-specific PCR amplification caused by non-specific priming. The U.S. Pat. No. 5,792,607 (Backman et al) describes a method using EndoIV to unblock primers for PCR and ligation reaction. But because the activation of primers using EndoIV is very slow (minutes instead of seconds), it is impractical to use this method to amplify DNA exponentially. Also, the Backman patent only describes EndoIV derived from *E. coli* and only mentions that the method should work better if using thermostable EndoIV. The method described by Backman et al. has not been commercialized.

Recently IDT (Integrated DNA Technologies) published methods and made reagents available for RNAse H-dependent PCR (rhPCR, patent application US 2009/0325169; Dobosy et al., *BMC Biotechnology* 2011, 11:80). The authors describe a method using primers with blocked 3'-ends and containing a single RNA base close to the 3'-end. Primer activation occurs if a thermostable RNAseH enzyme cleaves the annealed primer at the RNA base, generating a 3'-OH, thereby making the primer extendable by polymerase. The rhPCR makes PCR more complex as it requires an additional thermostable enzyme, RNAse H, that is currently commercially available only from IDT and Epicentre. Also, an RNA base in the primer requires a more complex manufacturing and can double the cost of primer compared to a regular DNA oligo. For example, a list price per base at the 100 nmolar scale is $0.55 and $6.50 per base for DNA and RNA bases, respectively (IDT Technologies).

Next generation sequencing (NGS) often requires enrichment of regions of interest in the genome or transcriptome. PCR, single-plex or multiplex, is one of the methods frequently used for enrichment, for example, AmpliSeq from Life Technologies. There are three major challenges in multiplex PCR enrichment for NGS: 1) formation of primer-dimers; 2) carry over contamination; and 3) PCR-errors.

1. Primer Dimers: Primer dimers can consume a lot of reagents as short primer dimer amplicons tend to be amplified very efficiently and dominate the PCR reaction.
2. Carry over Contamination: The high cost and sequencing throughput of NGS, where millions of sequences are generated in a single run, results frequently in multiple samples with different bar-codes being combined and processed together on the same plate or strip. Opening reaction tubes after PCR can result in a few amplicons being transferred through aerosols into other reaction tubes; this is called carry over contamination.
3. PCR Errors: Polymerases tend to make errors during PCR (most frequently mis-incorporation of nucleotides) and, if these errors occur during early cycles they appear as "mutations" in NGS. Molecular bar-codes called degenerate base regions (DBR; see J. Casbon, S. Brenner et. al "Increasing confidence of allele calls with molecular counting," U.S. Pat. No. 8,481,292, and U.S. patent application Ser. No. 13/853,981 "Method for accurately counting starting molecules") are random sequence tags that are attached to molecules that are present in the sample. These tags allow one to distinguish PCR errors during sample preparation from mutations that were originally present in the sample.

Previously Bi and Stambrook, ["Detection of known mutation by proof-reading PCR"; Bi and Stambrook, *Nucleic Acids Research*, 1998, Vol. 26, No. 12 3073-3075] and Lin-Ling et al. ["Single-base discrimination mediated by proofreading inert allele specific primers"; Lin-Ling et al., *J Biochem Mol Biol*. 2005 Jan. 31; 38(1):24-7] described how exo+ polymerases remove mismatched bases at the 3'-end. They specifically teach this as a genotyping or mutation detection method. Mutations are amplified by wild type specific primers that have a non-Watson-Crick base pair at the 3' ends that are cleaved and extended; primers that perfectly match wild type are not cleaved and thus not extended. Similarly, PCT/US2005/010782 "Quantitative amplification with a labeled probe and 3' to 5' exonuclease activity" by Bin Li et. al. specifically teaches that the 3' most "N residue represents a mismatch to the target nucleic acid sequence". Also, patent EP 2324124 "Proofreading primer extension" by Fiss and Myers teaches that extension during PCR happens "if the 3' portion of the oligonucleotide is not 100% complementary to the template nucleic acid". The "proof-reading PCR" is rarely used in practice as seen by its low citations number: 36 citations for Bi and Stambrook and 5 for Lin-Ling (Google Scholar, January 2014).

The idea of combining tagged target specific and universal primers is known; see, for example, application PCT/US2010/029854 by May et al. "Multi-primer amplification method for bar-coding of target nucleic acids". The "four primer amplicon tagging" method developed by Fluidigm uses closed tube amplification to incorporate sample bar codes for next generation sequencing (NGS) enrichment. But the method works only for singleplex PCR: each well has a pair of target-specific primers and a pair of universal, thus the name "four primer". Fluidigm also offers 10-plex PCR enrichment, but it is an open tube protocol: bar coded primers are added after multiplex PCR. Recently, similar methods were published for NGS enrichment using 60-plex 4 nM 5'-tagged primers for 6 PCR cycles and then 2 μM universal primers are added (Nguyen-Dumont et, "A high-plex PCR approach for massively parallel sequencing," *Biotechniques*, 55, pp 69-74, 2013). Nguyen-Dumont et al. also review different methods for NGS enrichment.

The primer concentrations are 50 to 1,000× lower than the 50 nM-1 µM used in traditional PCR. Low primer concentrations decrease the chance of primer dimer formation proportionally to the square of primer concentrations. However, concentrations of 5 nM and below generally do not generate a sufficient amount of PCR products to observe a signal in qPCR or a band on a gel.

Due to the above-noted drawbacks of current strategies to prevent non-specific amplification during PCR, e.g., specificity, cost, manufacturing logistics, and the like, there is a need for more specific, flexible, and cost-effective methods of PCR nucleic acid detection. The present invention meets these and a variety of other needs.

SUMMARY OF THE INVENTION

The present invention generally provides methods and compositions for overcoming non-specific PCR amplification caused by non-specific priming. Methods of the present invention include the use of tagged, target-specific primers that are blocked, in combination with universal primers. A variety of strategies for activating blocked primers are provided. The present invention is broadly applicable to any PCR, but is more important when PCR is multiplexed: more than one DNA target is amplified in the same reaction. The methods and compositions described here can be used for both qPCR (aka real-time PCR) or end-point PCR when the products of PCR are further analyzed by sequencing, fragment sizing and other methods known in the art. The primary use of the present invention is for PCR based detection methods, but can also be used for ligation-based detection methods.

The present invention combines the idea of using blocked primers that are unblocked during PCR after they anneal to their templates. Described herein are novel methods to unblock the primers. In one aspect of the invention, one method to activate blocked primers is using a polymerase with 3'-exonuclease (exo+) activity to remove a blocking moiety at the 3'-end of primers. The results demonstrate that Endonuclease IV can cleave 5' from an internal C3 spacer and that 3'-exonuclease activity of a thermostable polymerase can cleave off a 3'-C3 blocker when 3'ends of primers form a perfect Watson-Crick pairing with the templates. The methods of the invention combine the use of blocked primers (extendable after activation as described above) with the idea of using tagged target specific and universal primers in a closed tube reaction. It is very difficult to perform highly multiplexed reactions in a closed tube when regular unblocked primers are used: these primers form primer dimers that tend to dominate the amplification. Blocked primers are extremely resistant to primer dimer formation, thus enabling high multiplex PCR.

In another aspect of the invention, to overcome the low activity of EndoIV, the methods employ a two-step four-primer PCR: this approach requires EndoIV activity only for the first one or two cycles; in subsequent cycles unblocked universal primers continue PCR.

Described herein are methods and compositions that utilize 3'-blocked primers that cannot be extended by a polymerase activity only during PCR. Primers with the blocked 3'-end cannot be extended before an enzyme cleaves off the blocked 3'-end. The enzymes used to activate primers have dsDNA specificity: they require that primers are stably annealed to the complementary DNA. Thus it is unlikely that activation occurs during very brief non-specific primer annealing to each other or non-target sequences. This should dramatically decrease the chance of primer dimer formation and non-specific amplifications. Interactions between primers (that cause primer dimers) and potential mispriming sites are too brief for two enzymatic steps to occur: 1) blocking group removal and 2) polymerase extension. These blocked primers enable higher PCR multiplex as primer dimer formation is greatly diminished. In addition, these primers have a lower chance of non-specific priming.

These blocked primers can be activated sufficiently (time and quantity) to yield the desired amounts of amplicons during a regular PCR reaction using two target-specific primer for each locus (no universal primers), typically 20-45 or more cycles. However, our main emphasis is on applications where the blocked primers are comprised of two or more specific portions. For example primers may consist of a target-specific sequence at the 3'-end and one or more universal sequences at the 5'-end (5' tags). The target-specific sequence will amplify the desired target during the first few cycles. The amplicons generated in the first few cycles will then be further amplified in all subsequent cycles with universal primers matching the 5-tags of the primers. Two cycles are required, if both target specific primers are blocked, but only one single cycle is needed if only one primer is blocked. Universal primers that prime on these universal tags drive the PCR after one or two cycles, respectively.

Herein described are methods comprising the use of blocked primers comprising an abasic site, e.g., 3' 1',2'-Dideoxyribose (aka dSpacer or tetrahydrofuran) or C3 spacer. The annealed primers are cleaved at the 5'-side of the abasic site by commercially available thermostable Tth EndoIV from NEB (New England Biolabs) leaving a 3'-OH group which can be extended by polymerase. In addition, the inventors demonstrate that DNA polymerases that have 3'-exonuclease activity can activate and extend blocked primers by removing the 3'-blocking group, e.g., C3-spacer. In this case a single enzyme with 3'exonuclease and polymerase activity is sufficient to generate a PCR product. Alternatively, a separate enzyme with 3'-exonuclease activity and a polymerase can be used.

One can also use a separate "enhancer" oligo downstream from the 3'-blocked primer, so that there is a stretch of dsDNA on both sides of the blocking site; a preferred substrate for endonuclease IV. In still another aspect of the invention, methods and compositions to decrease primer dimers and non-specific amplifications are employed, using decreasing primer concentrations to 5 nM and below, e.g., 1 nM. Low primer concentrations decrease the chance of primer dimer formation proportionally to the square of primer concentrations. Concentrations of 5 nM and below generally do not generate a sufficient amount of PCR products to observe a signal in qPCR or a band on a gel. Therefore, 5' tags are added to the target-specific primers and regular universal PCR primers matching these tags are added to the PCR reaction. These universal primers are present in concentrations traditionally used in PCR typically ranging between 100 nM to 1 mM, typically >40-fold higher than the target specific primers. During the early PCR cycles with relatively long annealing time, low concentration target-specific primers initiate amplification. Alternatively, the methods of the invention use several PCR cycles with high annealing temperature, e.g., 68-72° C. that favors annealing and extension of long target-specific primers that have 5'-tags (tails). Then, the annealing time is shortened and optionally the annealing temperature is lowered to a more typical range of 58-64 C, where universal primers present at high concentrations (0.1-1.0 µM) drive the reaction and generate sufficient amplification to observe a qPCR signal or use amplified product for an end-point read out including sequencing using NGS.

Described herein are examples of using blocked primers for regular qPCR, multiplexed mutation detection using qPCR and PCR for NGS enrichment. Two examples of qPCR detection are shown using universal hairpin 5'-nuclease assays: single-plex for *Enterococcus* and multiplex for model EML4-ALK gene fusions. For closed tube EML4-ALK, 60× lower concentration of target-specific (5 nM) than universal primers (300 nM) were used. Described herein is a closed tube NGS enrichment method that can incorporate both unique molecular bar-codes (DBR) and sample bar-codes in a closed tube PCR. This method is not only quick and simple, but also minimizes the chance of carry over contamination between samples. Further described herein is a method to normalize (make similar) the amounts of different amplicons in a PCR reaction by slowing down cooling at late PCR cycles.

In another aspect of the invention, a method is used to design and use 5'-tailed target-specific primers that detect closely spaced mutations. The PCR cycling protocol uses high annealing temperatures, typically from cycle 3 onward, so that the mutation-specific primers that were extended during the first cycle and were complemented during the second cycle will preferentially anneal to those amplicons based on their increased melting temperature (Tm): both target-specific part of the primer and the 5'-tail contribute to primer annealing. Primers that were not extended in the first cycle will have a lower chance to anneal/extend starting cycle three because amplicons do not match their 5'-tails. One can then increase annealing temperature beginning with cycle 3 so that the temperature is too high for the allele-specific primers that did not extend at cycle 1. Alternatively, one can employ a high annealing temperature during the first two cycles, so that the allele specific primers are barely priming, and the same high annealing temperature is used after cycle two, so that tagged primers that extended at cycle 1 prime efficiently using 100% of their lengths, including tags, but competing allele-specific primers do not.

In a still further aspect of the invention, methods are described herein to improve sensitivity of detection of closely spaced mutation using rhPCR/qPCR with several blocked mutation-specific primers. Each mutation-specific primer carries a different tag next to its target-specific 3'-region, so that the primer that was extended in the first PCR cycle gains a thermodynamic advantage (higher Tm) starting cycle three over other mutation-specific primers specific for adjacent mutations. This approach is demonstrated using the methods to detect six mutations in codon 526 of rpoB gene in *Mycobacterium tuberculosis* (MTB): all six mutations cause resistance to rifampicin. The inventors used two sets of universal tags: one for six drug resistance mutations, so that FAM-dye signal in qPCR will indicate that at least one of these mutations is present in the sample, thus detecting all six mutations together. The second set of universal tags detects control region of MTB using HEX dye, so that the difference between FAM and HEX signals is used to make resistance or "no resistance" call.

The enrichment for sequencing, including NGS, for regions of interest, usually targets areas known for polymorphisms and mutations in human genes, is a rapidly growing application that is used for genetics and cancer diagnostics. Polymorphisms in BRAC1/BRCA2 genes are the most well-known example of germline (inherited) changes that have clinical significance. Somatic mutations in EGFR, BRAF, KRAS, and other genes are used for targeted cancer treatment (companion diagnostics). Advances in NGS technologies and its broad use in clinical research will rapidly expand both genetic and somatic mutation testing. The methods we describe will make both applications more robust and simpler to implement for clinical research and diagnostics use, including laboratory developed testing (LDT).

In one aspect of the invention, a PCR reaction mixture is provided comprising: (a) at least one pair of target-specific primers comprising universal 5' tags, where at least one target-specific primer cannot be extended by polymerase (3'-blocked primer); (b) at least one pair of universal primers that can prime on the universal 5' tags; (c) an enzyme that unblocks the 3'-blocked primer after it anneals to the target DNA generating a 3'-OH end; and (d) a polymerase that extends unblocked primers during one or more initial PCR cycles; and subsequently extends universal primers driving amplification in a closed tube reaction. Preferably, multiple blocked target-specific primers in the PCR reaction mixture amplify multiple targets (multiplex PCR), and target-specific primers for targets that are to be detected together comprise the same universal tags, and optionally blocked target-specific primers for targets to be detected separately comprise different universal tags; more preferably, universal primers and optionally universal probes are labeled and different universal primers and optionally probes are used to detect targets by priming on the different universal tags of the amplicons generated by the blocked primers. Said reaction mixture may be used for PCR enrichment for sequencing, wherein at least one of the universal primers comprises a sample bar-code that enables sample pooling for sequencing; and optionally wherein the blocked target-specific primers comprise random molecular barcodes allowing identification of individual DNA strands amplified in PCR, such that the first two PCR cycles incorporate random molecular bar-codes for each DNA strand present in the sample.

Preferably, the concentration of the target-specific primers in the reaction mixture is at least 40-fold less than the concentration of the universal primers; and/or the one or more 3' blocked primer(s) comprise(s) a C3 spacer(s) or another 3'-blocking modification. Preferably, the reaction mixture comprises a DNA polymerase with 3'-exonuclease activity or an endonuclease to unblock the primers. Optionally, the reaction mixture comprises a blocked primer comprising an abasic site to anneal to the target on both sides of the abasic site, and an endonuclease IV to cleave 5' from the abasic site, unblocking the primer; or comprises a primer comprising at least one RNA base, and further comprises an RNase H enzyme for unblocking the primer.

In a second aspect of the invention, a multiplex allele (mutation) specific PCR reaction mixture is provided to detect two or more closely spaced mutations, comprising: (a) mutation (allele) specific primers for each mutation to be detected, wherein the primers comprise the same target-specific 3'-regions, except for different 3'-ends; and (b) the primers of (a) further comprising different non-target-specific 5' tags; such that after the first two PCR cycles the first allele-specific primer that was extended in the first PCR cycle continues PCR by annealing to the amplicons that are 100% complementary to the whole first primer, but other allele-specific primers with 5'-tags not matching the amplicons generated by the first primer do not anneal at the annealing temperature used in PCR. Preferably, the allele (mutation) and target-specific primers of (a) and (b) further comprise universal 5'-tags and the different non-target specific tags of (b) are situated between the 3'-target-specific region and the universal 5' tags of the allele specific primers;

and the reaction mixture further comprises (c) at least one pair of universal primers that can prime on the universal 5' tags; more preferably, at least one of the allele or locus specific primers is blocked.

In additional embodiments of the invention, a PCR reaction mixture comprises at least one 3'-blocked primer comprising a 3'-end having a nucleotide sequence 100% complementary to a template; and either a polymerase with 3'-exonuclease activity, or a separate 3'-exonuclease and a polymerase; such that after the 3'-blocked primer anneals to the template the exonuclease unblocks the primer(s) and the polymerase extends the unblocked primer(s) during PCR.

The invention further provides a blocked PCR primer and an enhancer 3'-blocked oligo that anneals downstream from the blocked primer, forming no gap or a single base gap between the primer and the oligo when both are annealed to the target in a PCR or isothermal amplification mixture comprising an endonuclease that cleaves off a cleavable group at the single base gap and enables primer extension.

In a further aspect of the invention, methods are provided to detect or enrich target nucleic acids in a sample in a closed tube reaction, comprising the use of PCR with one or more 5' tagged target-specific primer(s) with a blocked 3'-end and universal primers that optionally comprise blocked 3' ends; that can prime on these universal tags, and optionally probes; such that during initial PCR cycles, the target-specific primer anneal, get unblocked and extend on target DNA, and in subsequent PCR cycles, the universal primers drive PCR. Optionally, the PCR reaction is normalized by slowing down cooling from melting to annealing temperature during late PCR cycles, such that the majority of abundant target amplicons reanneal and do not amplify, but rare ones continue their amplification. Preferably, the readout for the detection of nucleic acids is real-time or endpoint PCR for sequencing, NGS enrichment, fragment sizing using electrophoresis, surface hybridization, amplicon melting, molecular weight determination via electrophoresis or mass spectrometry.

Preferably, the one or more 3' blocked primer(s) comprise(s) a C3 spacer(s) or another 3'-blocking modification; more preferably, the method comprises the use of a DNA polymerase with 3'-exonuclease activity or an endonuclease to unblock the primers; or comprises the use of a blocked primer comprising an abasic site to anneal to the target on both sides of the abasic site, and an endonuclease IV to cleave 5' from the abasic site, unblocking the primer. In one embodiment, the method comprises the use of a primer comprising at least one RNA base, and further comprises the use of RNase H enzyme for unblocking the primer.

The methods can be used for PCR enrichment for sequencing, wherein at least one of the universal primers comprises a sample bar-code that enables sample pooling for sequencing; and optionally wherein the blocked target-specific primers comprise random molecular barcodes allowing identification of individual DNA strands amplified in PCR, such that the first two PCR cycles incorporate random molecular bar-codes for each DNA strand present in the sample.

In a further aspect of the invention, methods are provided for using PCR to detect two or more closely-spaced mutations with increased sensitivity, comprising the use of mutation-specific primers for each mutation with 5'-non target tags different for each primer, such that after first two PCR cycles, an increased annealing temperature is used to decrease completion between different mutation-specific primers, thus increasing assay sensitivity.

In a still further aspect of the invention, PCR amplification methods are provided comprising the use of at least one blocked PCR primer with a 3'-end complementary to the template, such that unblocking is performed by a 3'-exonuclease activity and extension by a polymerase activity, respectively, and wherein the two enzymatic activities are performed by a single enzyme or two separate enzymes The methods and compositions summarized above are described in detail hereinbelow.

DETAILED DESCRIPTION

Multiplex PCR or ligation can be used for multiplex encoding reaction for detection that we described previously (U.S. patent application Ser. No. 12/931,803). Here we describe a closed tube PCR using blocked primers. It is generally run as a multiplex PCR that includes 5' tailed target-specific primers at low concentrations and universal amplification or detection primers [probes] at regular concentrations. One can also add universal primers after, say 2 cycles of PCR with target specific primers, but this is less advantageous because this extra step requires opening a tube and active polymerase present in the reaction mixture can quickly generate non-specific amplicons if the temperature drops below the annealing temperature used in PCR.

Figure 1:
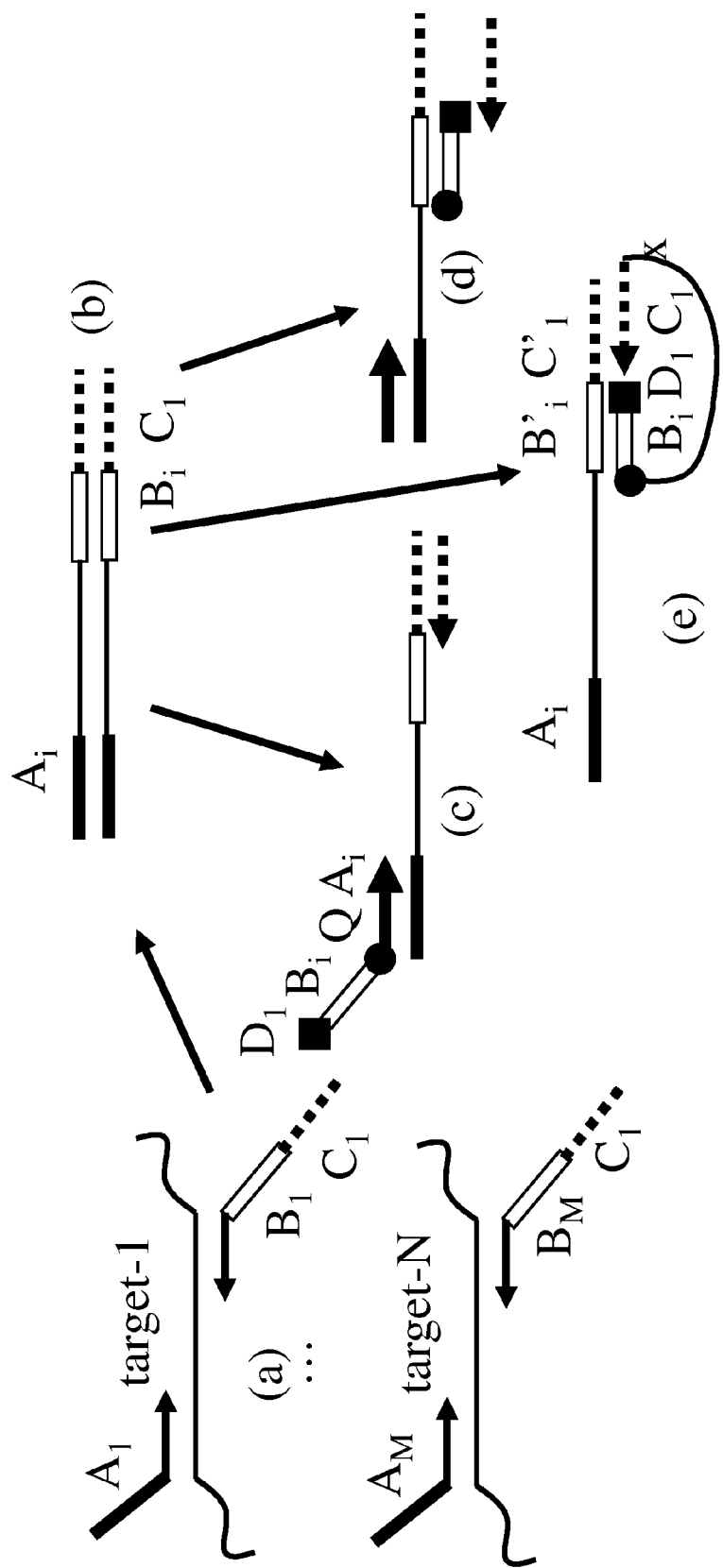
FIG. 1. PCR/qPCR closed tube schema. (a) Multiplex PCR encodes for targets by incorporating universal tags for each nucleic acid target: Ai, Bi and Ci where i=1 to M are used for N targets; N≥M. (b) Tagged amplicons. Detection using (c) universal hairpin (e) circle and (d) 5'nuclease (TaqMan™) assays. If no probe is used, the PCR reaction can be used for NGS enrichment and Bi tags can be molecular bar codes. Target-specific 3' ends of primers are shown as black arrows. "Primes" indicate complements: e.g., $B'_1$, is complement of $B_1$.

Multiplex PCR is also used for so called "pre-amplification" to amplify targets from small samples, e.g., single cells, or for qPCR detection in very small volumes in droplets or nanowells. Multiplex PCR is also used as a target enrichment method for NGS. For example, AmpliSeq from Life Technologies uses 1,536-plex PCR or even ~20,000 plex for enrichment. Conventional wisdom indicates it is impossible to avoid primer dimer formation and indeed the protocol for AmpliSeq requires a step to separate long target-specific amplicons from short primer dimers. This additional clean-up step makes the NGS sample prep workflow more complex; in addition non-target amplifications, e.g., primer dimers, consume PCR reagents reducing the yield of target specific amplicons. Described herein is a multiplex PCR method using primer concentrations of 50 nM, 5 nM, 1 nM or less. The schematics are shown in FIG. 1. Each 5'-tailed target specific primer in FIG. 1 is present at concentrations of 5 nM, 1 nM or less. During the first 2 to 6 cycles, the disclosed methods use relatively long annealing times (typically 2-15 minutes) so that these low concentration primers have sufficient time to anneal to their targets. After two cycles, PCR will generate amplicons that have universal tags at both ends. Now, one can use regular PCR conditions with short annealing times, e.g., 1 minute or less. Short annealing times decrease the likelihood that low concentration target-specific primers will have sufficient time to anneal to the amplicons; the higher concentration universal primers (FIG. 1 c, d) have a kinetic advantage and dominate detection at later stages of the PCR amplification. One can also help to shift the balance towards the universal high concentration primers by using the maximum ramp speed of the thermo cycler to cool from 95° C. to the annealing temperature. This closed tube multiplex tag-PCR amplification has several advantages over traditional multiplex PCR including 1. Very low primer concentrations allow high multiplex;
2. A lower chance of primer dimer formation that is proportional to the square of primer concentration;
3. Amplicons that are to be detected together, e.g., sequences by an NGS, can use the same tags, but those that are to be detected separately can use different tags. For example, in case of qPCR detection (FIG. 1 c, d) different dyes measure the cumulative presence for each set of targets that use the same tags.
4. 1-step tag-PCR permits UDG contamination control that is traditionally used in diagnostics and other PCR applications avoiding sample cross contamination issues associated with preamplified DNA.

EXAMPLE

Figure 2:
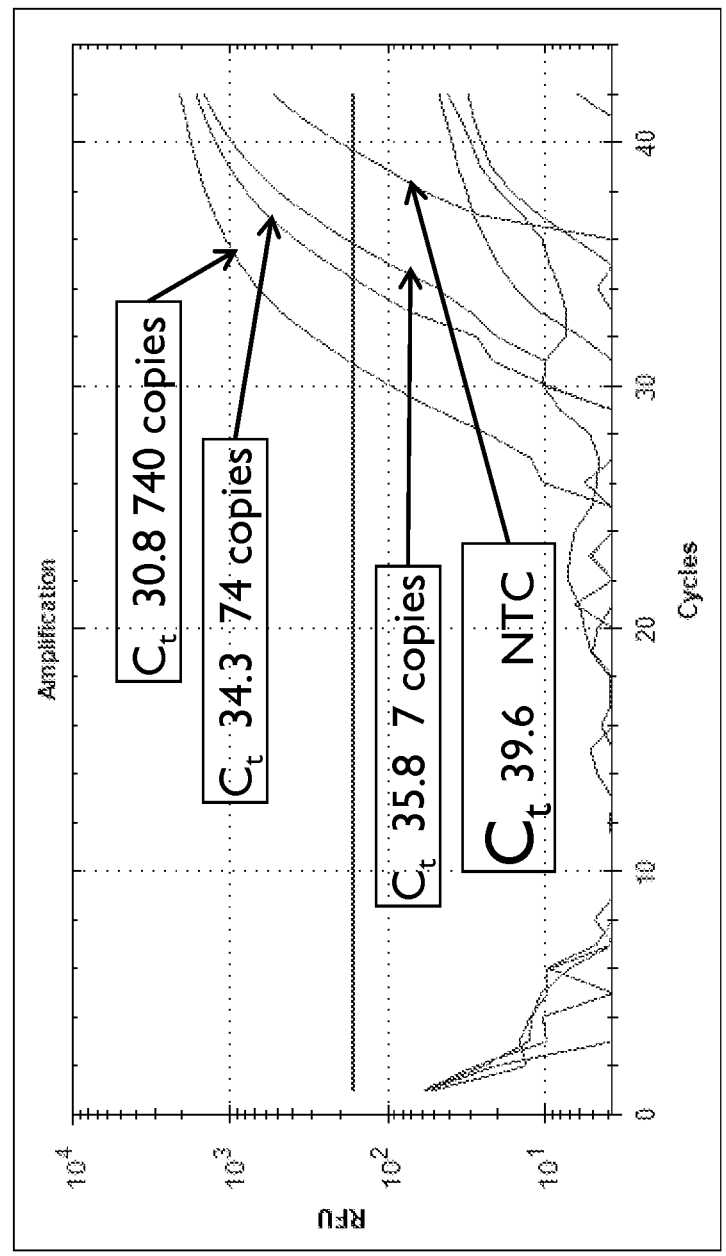
FIG. 2. An example of a closed tube UniTaq qPCR to detect varying amounts of Enterococcus gDNA. Four primer pairs including two Enterococcus specific primers (5 nM) and UniTaq detection primers (600 nM). Amplification curves for 700, 70 and 7 copies of Enterococcus and NTCs are shown. The delta Ct between 10× dilutions approximates 3.3, the expected optimal theoretical amplification efficiency. PCR amplification buffer was 1×PCR Environmental Master Mix (Life Technologies).

The inventors have used a closed tube qPCR to detect *Enterococcus* gDNA from water samples. In the case of *Enterococcus* a 16S DNA-specific assay at 5 nM was used. FIG. 2 shows amplification curves for 700, 70 and 7 copies of *Enterococcus* and NTCs. Each qPCR reaction contained four primers: two target-specific primers for 16S gDNA with 5' tails and two universal UniTaq primers as shown in FIG. 1c. The delta Ct between 10× dilutions is close to 3.3, the expected optimal theoretical amplification efficiency. The non template control (NTC) reaction is also shown.

Figures 3A, 3B:
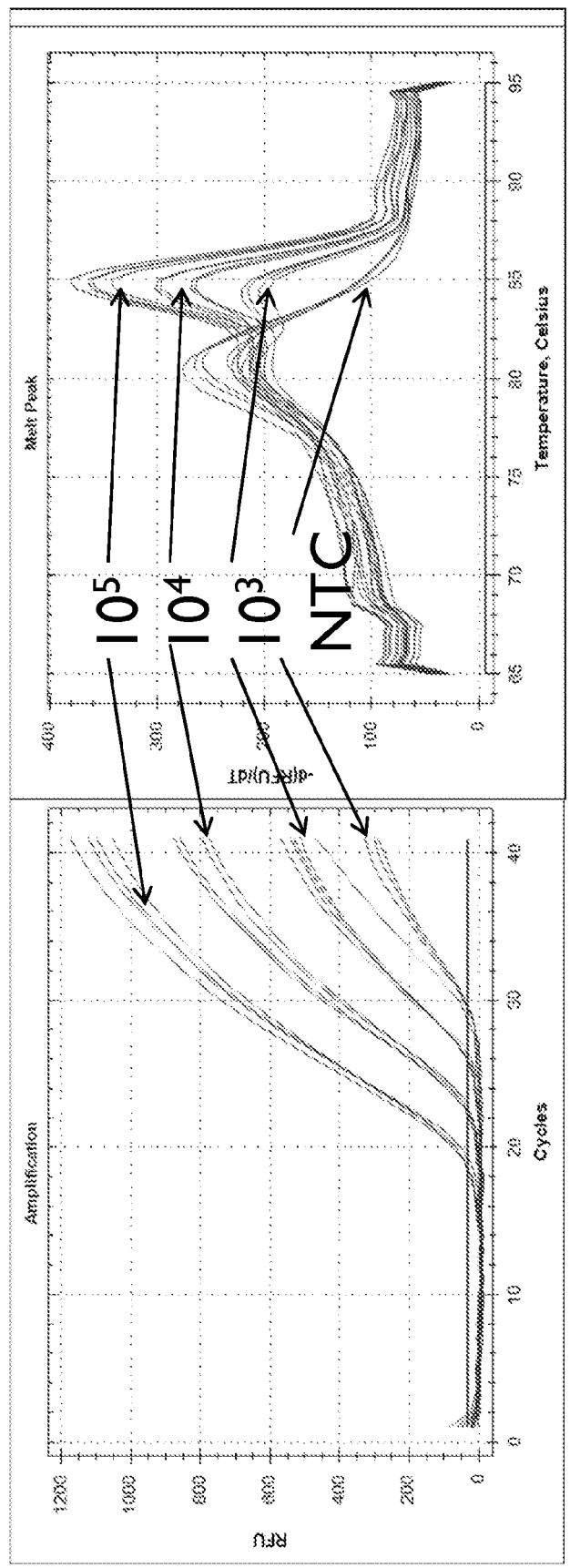
FIG. 3. An example of a closed tube reaction detecting artificial template (oligonucleotide) representing the ELM4-ALK fusion gene using rhPCR. (A) Amplification curves; (B) melt curves.

FIG. 3 shows a 1-step closed tube reaction where the sample consisted of $10^3$, $10^4$ and $10^5$ copies of an artificial template representing the ELM4-ALK fusion gene using rhPCR. Seven EML4 fusion specific rhPCR primers and exon 20 ALK rhPCR primers @ 5 nM (all primers had a single RNA base and 3'-C3 block) were multiplexed with universal FAM labeled and regular primers @300 nM (FIG. 4c). Amplification curves (a) and melt curves (b) are shown for 3 dilutions of EML4-ALK ATs and NTC. Amplification curves demonstrate a deltaCt ~3.33 is close to the theoretical PCR amplification efficiency (doubling in every cycle). The NTC signal has a lower Tm than the target amplicon.

Figure 4:
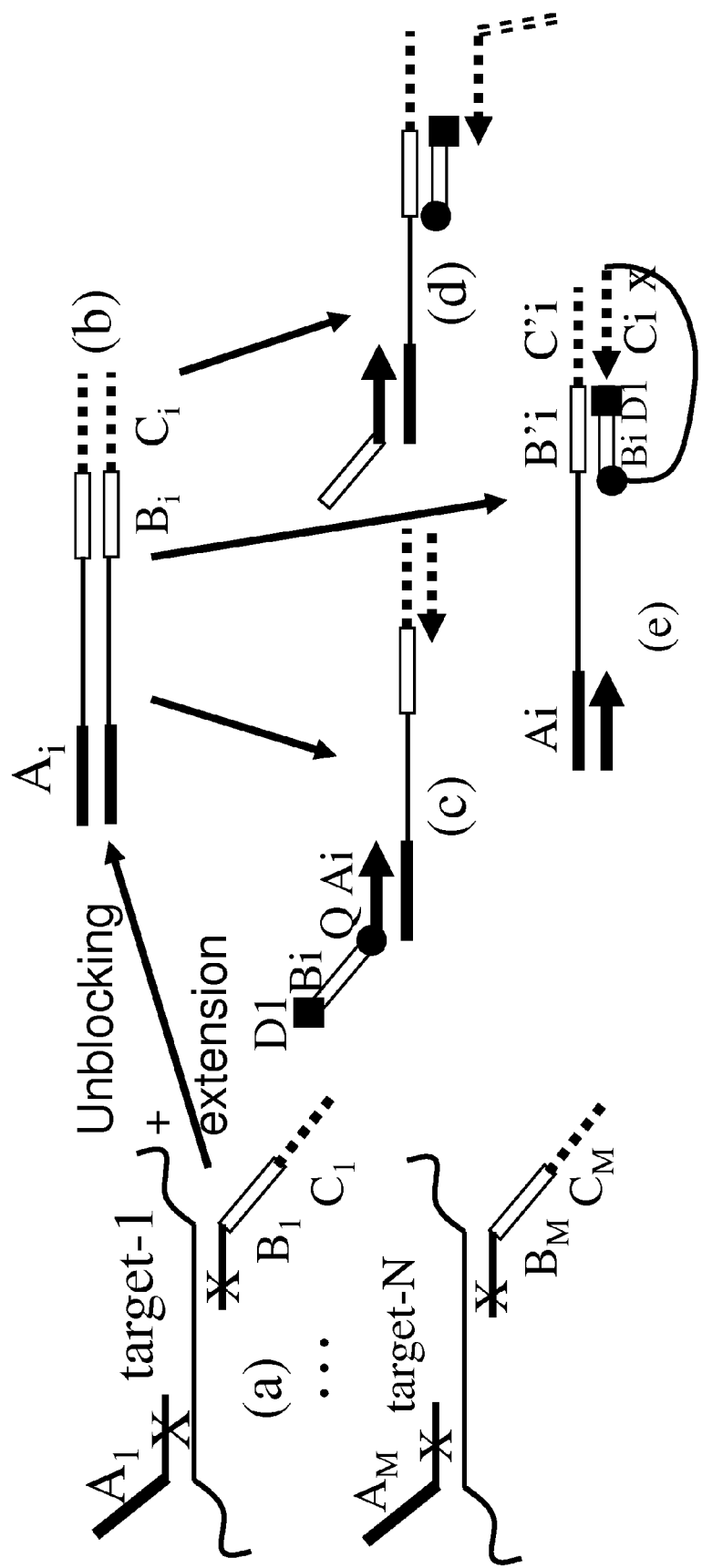
FIG. 4. PCR closed tube using blocked primers. (a) Multiplex PCR encodes targets by incorporating universal tags for each nucleic acid target: Ai, Bi and Ci where i=1 to M are used for N targets; N≥M. "X" indicates blocked primers (b) Tagged amplicons are generated by a combination of cleaving agent and a polymerase. Detection using (c,e) UniTaq and (d) 5'nuclease assays. In the absence of any probes the PCR reaction can be used for NGS enrichment; in this case M=1 and N can be any number between one and many thousands.

FIG. 4 shows schematics for multiplexing using blocked primers (FIG. 4a, "X" indicates a cleavable modification and lack of an arrow a blocked 3' end) that after unblocking and extension generate tagged (encoded) products (FIG. 4b). This encoding PCR can use the same (M=1) or different (M>1) universal tags (FIG. 4a). The encoded products can be detected using universal hairpin (FIG. 4c) or "circle" (FIG. 4e) methods described in the U.S. patent application Ser. No. 12/931,803. Alternatively, an optional universal probe can be used (FIG. 4d) to generate signal using universal primers with or without 5' tags (FIG. 4d shows both an optional probe and 5'-tags on universal primers). The two stages of PCR: 1. unblocking and extension of tagged target-specific primers and 2. amplification by universal primers can be performed in a closed tube reaction. Alternatively one can employ two separate steps: after at least two cycles of encoding the reaction can be optionally split into multiple reactions, universal primers/probes are added, and PCR is continued.

Figure 5:
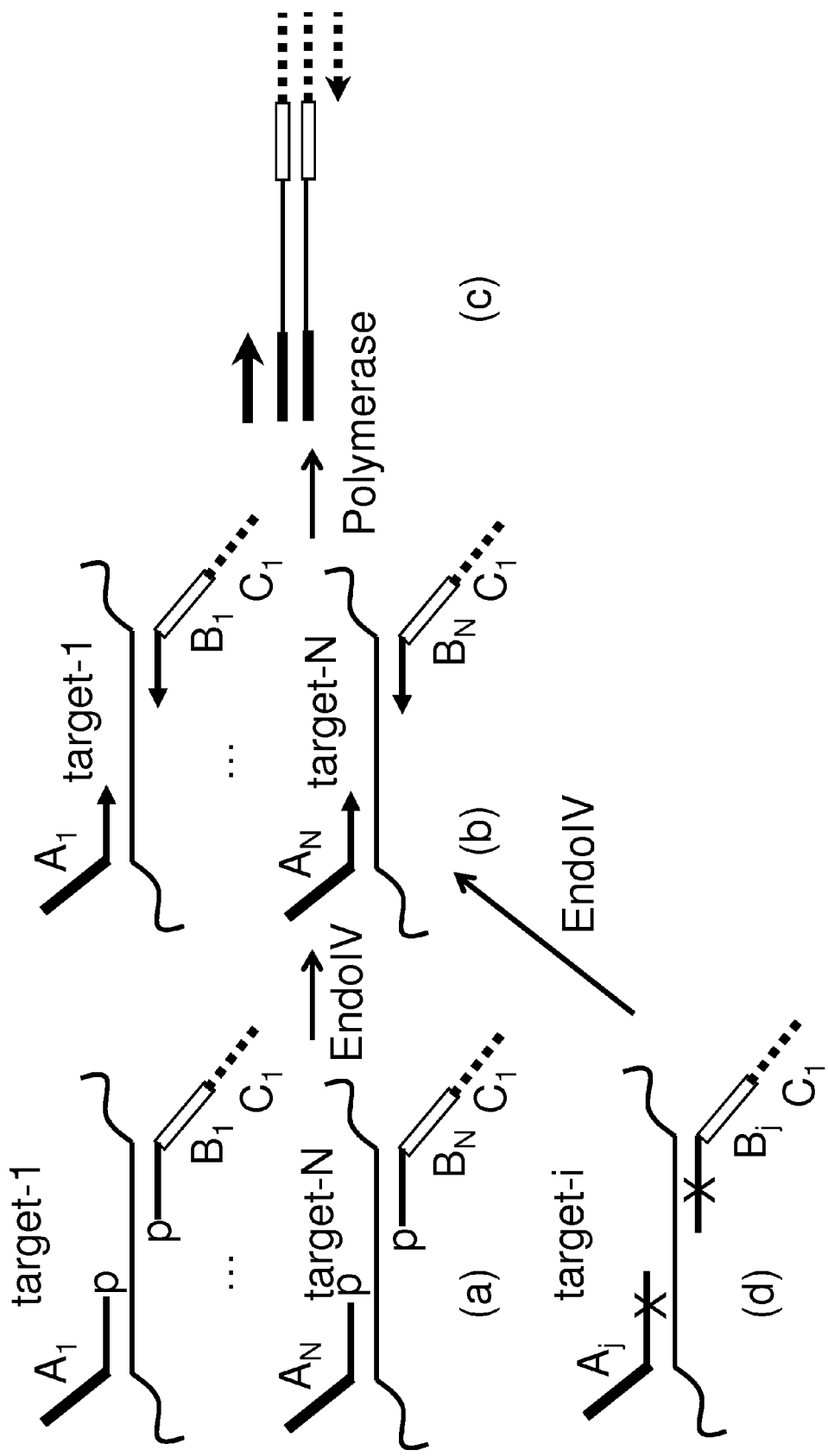
FIG. 5. Using 3'-phosphorylated blocked primers (a) and endonuclease IV to remove blocking 3'-phosphates. (b) After unblocking 5'-tailed target-specific primers are extended; (c) polymerase extends universal primers (thick and dashed arrows). (d) Similar approach that uses THF or C3 spacer ("X") that is cleaved off by the endonuclease.

FIG. 5 shows schematics of using endonuclease IV (EndoIV) for unblocking 3'-phosphates (FIG. 5a) or an internal abasic site, e.g., C3 or THF for multiplex PCR, e.g., for NGS enrichment. After unblocking (FIG. 5b) a polymerase first generates tagged amplicons that are amplified by universal primers (FIG. 5c).

With no primer dimers competing for PCR reagents, one can run more cycles of multiplex PCR and use a technique known as "$C_0t$" (DNA reassociation kinetics) at later cycles to normalize the amounts of PCR amplicons. The $C_0t$ method uses an additional temperature holding step when cooling from 95° C. to the annealing temperature at late cycles of the PCR. The holding temperature (between 75° C. and 80° C. for 10 sec to 2 min) is chosen to be much higher than the Tm of the primers, but lower than the melting temperature of the amplicons, so that the complementary strands of the more abundant PCR products reanneal and stop being amplified whereas lower abundance products continue to be generated.

In principle, two PCR cycles that use encoding primer are sufficient to incorporate the universal tags; starting with cycle 3 universal primers can take over the amplification. However in some cases it is desirable to continue amplification using the target-specific encoding primers for additional cycles. For example when performing rhPCR/qPCR (using RNaseH for cleavage) additional cycles of rhPCR (target-specific) exponentially increase mutation detection specificity. In this case, we propose to use high annealing temperatures and long annealing times during early PCR cycles, e.g., 3-18. High annealing temperatures prevent the short universal primers from annealing, resulting in the tailed target specific primer to continue driving the reaction. For example, we used the following cycling protocol: (95° C. 5 min); (95° C.-15 s, 62° C.-2 min)×2 cycles; (95° C.-15 s-70° C.-2 min)×12 cycles; (95° C.-15 s-62° C.-45 s)×40 cycles.

As used herein, "endonuclease-dependent PCR" is PCR that contains Endonuclease to cleave primers. The inventors found that C3 spacers can be effectively cleaved by endonuclease IV (a DNA repair enzyme) leaving an OH-group at the 3'-end so the unblocked primer can be extended by a DNA polymerase. The inventors used thermostable Tth EndoIV from NEB. Thus, endonuclease-dependent PCR can not only use blocked primers with canonical abasic sites, e.g., tetrahydrofuran (THF), but also a C3 spacer. The C3 spacer is less expensive than THF and is used by IDT for rhPCR as a polymerase extension blockers, either at the 3'-end (GEN1 rhPCR primer design) or close to the 3'-end (GEN2 rhPCR primer designs).

Figure 6:
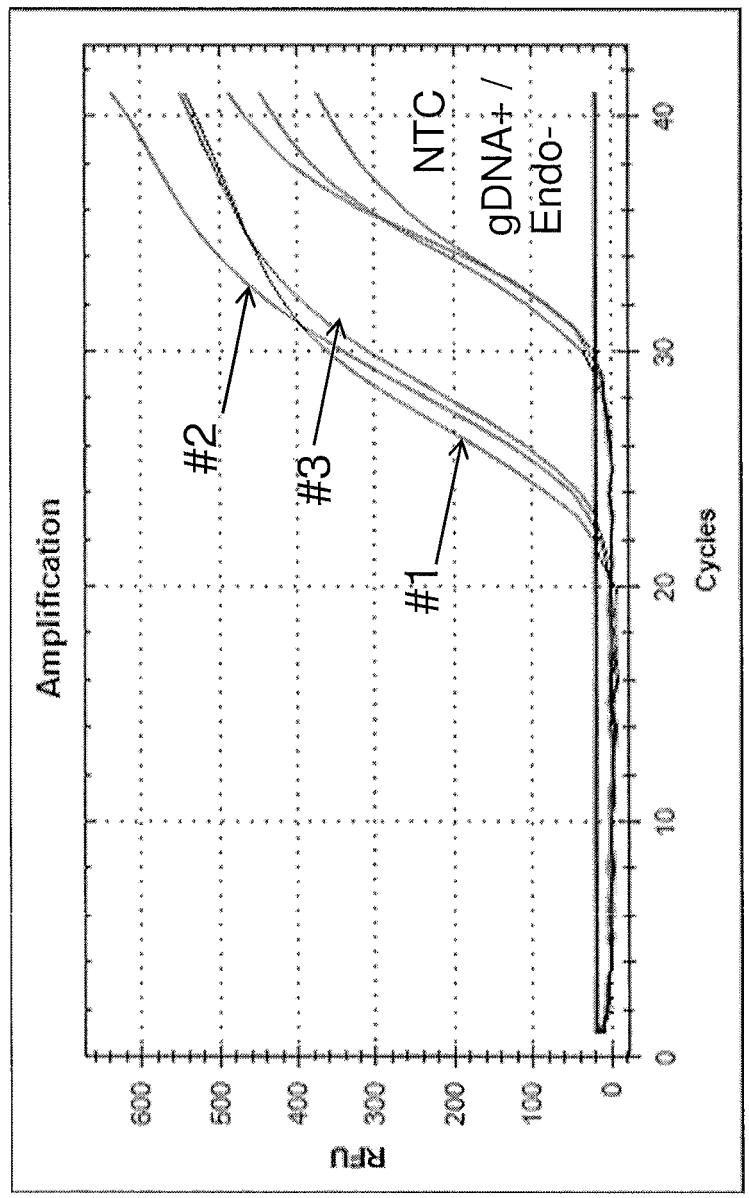
FIG. 6. Exonuclease-dependent PCR amplification curves. The three curves that show signal (lower Ct values) are for regular (#1), THF (#2) and C3 (#3) blocked primers with the same reverse primer #4 (at 5 nM). NTC (gDNA−) using regular primers and gDNA+/Endo− (wells with gDNA, but no endonuclease IV) using THF/C3 blocked primers give much lower signal. UniTaq method was used to generate signal.

FIG. 6. shows results for endonuclease-dependent PCR (with and without Tth Endo IV enzyme) comparing regular and blocked primers that contain a single THF or C3 spacer. The signal is similar for regular primers and THF/C3 endonuclease-dependent PCR. The NTC signal is also similar for regular primers and Endo-minus reaction that contains target DNA indicating that EndoIV cleavage is required for reaction. Tth EndoIV has a relatively low activity: 1 unit cleaves 1 ug (0.5 pMol) of partially depurinated plasmid DNA in 30 min, whereas 1 mU of RNaseH is sufficient to amplify 1 ng of plasmid in rhPCR using cycle times of 30 sec. Therefore we used 10 units in a 10 uL reaction and long extension times (20 min) during the first 2 cycles followed by fast cycling: 95° C. 5 min; (95° C.-15 s, 55° C.-10 min, 62° C.-10 min)×2 cycles; (95° C.-15 s-62° C.-30 s; 70° C.-15 s)×40 cycles. After EndoIV cleaves the blocked primers during the first 2 cycles the reaction is driven by universal primers in subsequent cycles. All target-specific primers were at 5 nM, the two universal primers were at 300 nM. It may be possible to shorten the annealing time for the first two cycles using higher activity endonuclease.

The experiments used one of the first 3 oligos as a forward primer: 1. control regular non-modified primer, 2. THF/idSp/, aka dSpacer and 3. C3/iSpC3/with a regular reverse primer (#4) at 5 nM in a close tube reaction with the universal detection primers (#5 and #6). The last oligo (#7) is an artificial template that was detected; all oligos are shown in Table 1.

TABLE 1

1. c1_RS1333_RM2204-1
   TGTGCCGAACGTGTACCAAtCCAATATGCCAGGTGCCATGGTGCTTCC
   GGCGGTAC
   (SEQ ID NO: 1)

2. c1_RS133_RM2204-152
   TGTGCCGAACGTGTACCAAtCCAATATGCCAGGTGCcatggcttgcag
   ctccTGGTG/idSp/TTCCGGCGGTACA/3SpC3/
   (SEQ ID NO: 2)

3. c1_RS1333_RM2204-155
   TGTGCCGAACGTGTACCAAtCCAATATGCCAGGTGCCATGGTGCTTCC
   GGCGGTAC/iSpC3/ctttaggtcctttcc/3SpC3/
   (SEQ ID NO: 3)

4. EML4_1725_46_RM2204-4
   TTGTCTCTGCGACCCATCAAGTGGAGTCATGCTTATATGGAGCAA
   (SEQ ID NO: 4)

5. RS600-RM2204Fz-87/
   56-FAM/TCCAATATG/ZEN/CCAGGTGCCA/ZEN/TTGTCTCTGCGA
   CCCATCAA
   (SEQ ID NO: 5)

6. RS133_RM2204I-40
   cgTGTGCCGAACGTGTACCAAt
   (SEQ ID NO: 6)

7. EML4_1725_at_c1I-153~10^5 copies of artificial template
   GTGGAGTCATGCTTATATGGAGCAAAACTACtGTAGAGCCCACACCtG
   GGAAAGGACCTAAAGTGTACCGCCGGAAGCACCAggagctgcaagcca
   tgca/3SpC3/
   (SEQ ID NO: 7)

Endonuclease-dependent PCR is similar to rhPCR developed by IDT, except using a different base modification (C3/THF vs. RNA) and a different cleavage enzyme: EndoIV vs. RNase H. One difference is that rhPCR is using only target-specific primers and therefore sufficiently active RNase H must be present during late cycles to drive the reaction when there is a very large number of amplicons being generated. When using Endo IV, enzymatic cleavage is required only during the first (if using only one blocked primer per target) or the first two cycles (if using both forward and reverse blocked primers). One can also use rhPCR with a very small amount of RNAase H enzyme, as its activity is only needed during early PCR cycles to cleave a small number of amplicons. Tth EndoIV has a low activity that is not sufficient to drive PCR at late stages, though endonucleases from different thermophilic bacteria, e.g., Pfu, may have a higher activity.

Endonuclease IV does not cleave single stranded DNA. Thus, a mismatch next to the cleavage site that causes a disruption in Watson-Crick base-pairing slows down cleavage. This can be used to detect mutations and SNPs. For example, one can use a mutation specific primer where the base next to the cleavage site targets a mutation. In case when the mutation-specific base is upstream of the cleavage site, there would be a mismatch at the newly generated 3'OH end of the primer. The specificity of the PCR will depend on two enzymatic steps: Endo IV cleavage at a mismatch and polymerase extension at the same mismatch; traditional allele-specific PCR depends only on the specificity of polymerase. In this case the specificity is determined by the first cycle; after mismatch extension the amplicon caries the "mutated" base from the primer. Cleavage next to a 3'-terminal phosphate (due to diesterase activity) with the 3'-base of the primer being specific to the mutation would be an example of the specificity of the assay being determined by two independent enzymatic steps in the first PCR cycle. It should be noted that the efficiency of endonuclease cleavage at the 3' end of a primer can be significantly increased by using an enhancer oligo downstream from the blocked primer, see Kutyavin et al., *Nucleic Acids Research*, 2006, 34, No. 19 e128. One can also use an enhancer oligo for endonuclease dependent PCR. In case 3'-blocked primer has 3'-phosphate the enhancer oligo can be abut with the 3'-blocked primer. In case a 3'-C3 block is used, there may be a single base gap between the 3'-end of the blocked primer and the 5'-end of the enhancer oligo. In both cases EndoIV is presented with dsDNA template and can cleave off the blocking moiety. Having mutation-specific base in the primer downstream from the cleavage site has single enzyme (endonuclease) specificity, but this specificity is exponential when blocked target specific primers drive the PCR: e.g., a 20% mispriming over 10 cycles generates a marginal amplification: $(1.2)^{10}$ is much smaller than $2^{10}$.

Figure 7A:
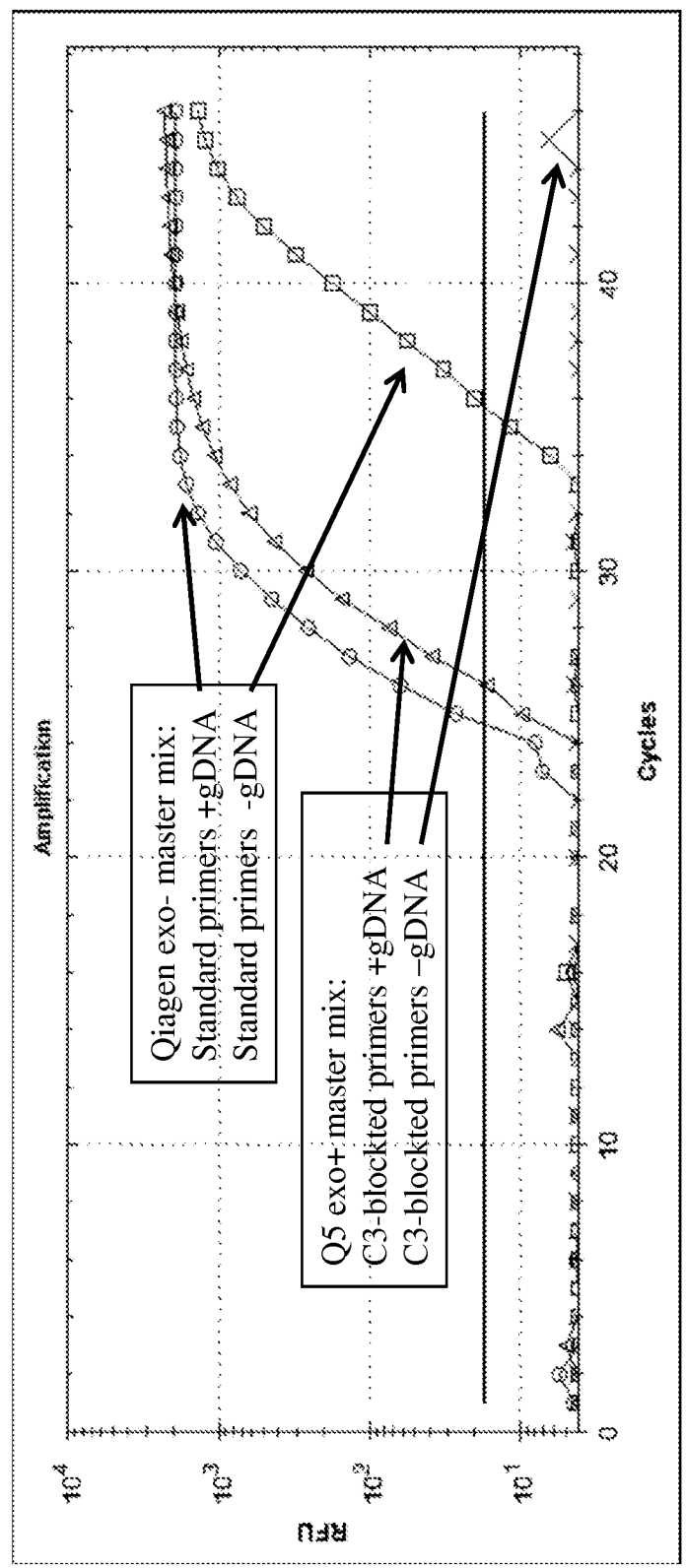
FIG. 7. Blocked and unblocked primer PCR of human gDNA. EvaGreen signal in qPCR (A) and melt curves after PCR (B) demonstrate that blocked primers are unblocked by the 3'-exonuclease activity of Q5 thermostable DNA polymerase from NEB but not by a DNA polymerase lacking 3-exonuclease activity (Qiagen Quantifast Multiplex PCR Kit). Also in the absence of any target DNA (NTC) no primer-dimer formation was observed in reactions with blocked primers (B), whereas reactions with regular primers show low Tm primer dimer peak (B) in the melt curve.
Figure 7B:
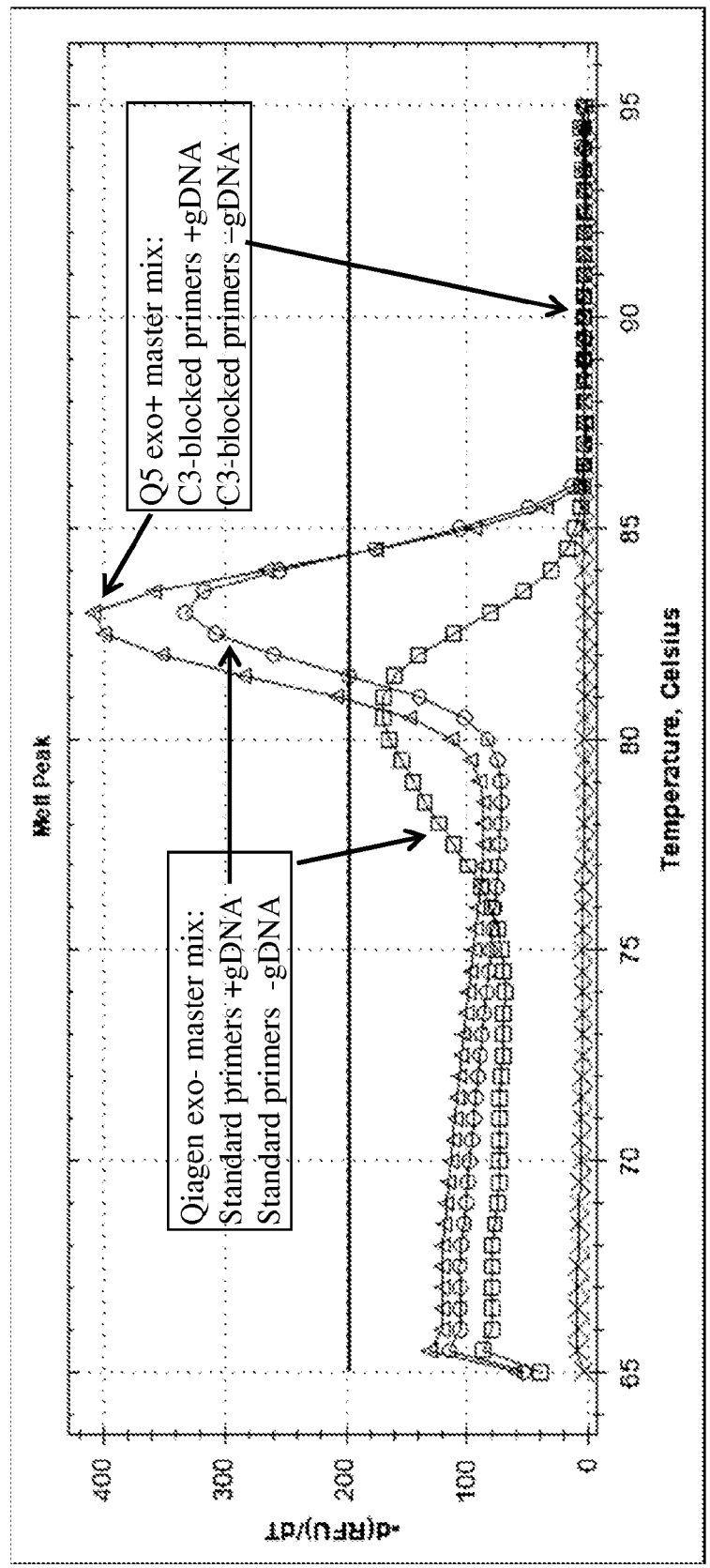

The inventors found that 3'-exonuclease (AKA proof reading) activity of polymerase by itself is sufficient to remove the 3'-blocking from primers even if the 3'-end is matching the template. In addition, this exo+ activity is sufficient to drive PCR at late cycles, so that one can run [multiplex] PCR without universal primers; blocked target-specific primers are cleaved efficiently enough to generate a detectable signal. FIG. 7 shows the performance of C3-blocked compared to regular primer pairs for the human gDNA GNAS complex on chromosome 20: EvaGreen signal in qPCR (FIG. 7*a*) shows amplification and melt curves of dsDNA PCR amplicons (FIG. 7*b*) indicate if desired gDNA (high Tm) or primer dimers were amplified (low Tm). As expected, polymerase with the 3'-exonuclease activity (Q5 from NEB was used), but not regular polymerase that lacks 3'-exonuclease activity generated signal using C3-blocked primers. In this experiment the C3-blocked primers were perfectly complementary to human gDNA. There is a small loss of PCR efficiency for blocked primers that have 1.5 cycles higher Ct than unblocked ones. The inventors observed that non-template control (NTC, no human gDNA, −gDNA) reactions do not form primer dimers (flat line in FIG. 7*b*), if blocked primers are used, but regular primer do generate low Tm~81 C melt curve indicating primer dimer formation. This experiment demonstrates that one can run regular two primers per locus PCR amplification (without universal primers) using blocked primers perfectly matching the target DNA using 3'-exo+ DNA polymerase.

Figure 8:
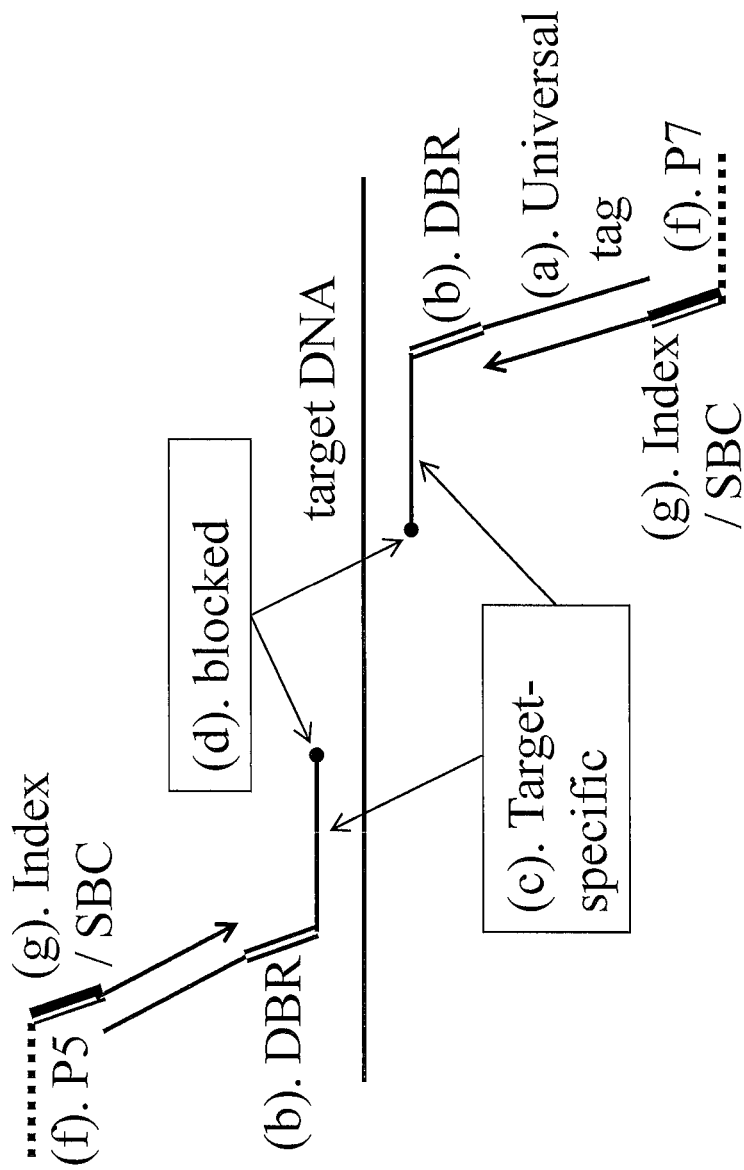
FIG. 8. The schematics of a closed tube NGS enrichment experiment. One primer pair is shown as an example of a multiplex. The target-specific primers consist of the following parts, starting at the 5'-end: (a) universal tag, (b) degenerate base region (DBR, optional), (c) locus/target-specific region, (d) blocked 3'-end and (e) optionally an additional cleavable site (not shown). Universal primers have these parts, starting at the 5'-end: (f) P5/P7 tags (Illumina surface tags; any tag supported by sequencing instrument can be used), (g) index/sample bar codes (optional) and (a) universal tags.

FIG. 8 shows the schema for the closed tube PCR enrichment for NGS using blocked primers. Multiple blocked primers at low 1 nM-50 nM concentrations are multiplexed together with universal primers. The target (locus) specific primers have universal tags and the 5' end and optionally DBR (see Casbon et. al)—random molecular tags. During the first two PCR cycles with long annealing times, typically between 1 and 15 minutes, primers at low concentrations have enough time to anneal to the target regions. The exonuclease unblocks the annealed primers and polymerase extends them. High fidelity polymerases (to minimize PCR errors) that have 3'-exonuclease activity are typically used for NGS PCR; so a single enzyme can perform both steps: primer unblocking and extension. Universal primers cannot anneal during the first two cycles because amplicons with regions complementary to universal tags are generated only at cycle 2. In case DBRs are used, each strand of DNA present in the sample acquires a pair of two unique molecular bar-codes at both ends of the amplicon. After 2 cycles the primer annealing conditions are shifted to a short annealing at a lower temperature, e.g., 10-60 seconds at 55-64° C. These conditions favor the annealing of the universal primers (present at high concentrations) over the target-specific blocked primers. Optionally, the universal primers can also be blocked. Depending on the number of amplicons in the multiplex and the desired sequencing depth, usually 4 to 96 (or more) samples can be pooled and sequenced together in a single lane. In this case universal primers may contain so called indexes or sample bar codes (SBCs), to identify each sample in the pool. Occasionally target-specific primers anneal and extend in later cycles (after cycle 2) incorporating a new DBR at one end of the amplicon. But it is unlikely that this would occur at both ends of the amplicon; one will still be able to match individual strands that were present in the original sample to reads using one of the two DBRs in each read. Small differences in efficiencies for different amplicons in multiplex PCR after exponential amplification can generate vastly different number of molecules for each amplicon (and different NGS coverage). The inventors propose a simple method to normalize PCR by slowing down the cooling from the melting to the annealing temperature at late PCR cycles. Starting cycle 20 (the starting cycle depends on the initial amount of amplifiable DNA) a 80° C. degree step typically between 15-sec and 2 minutes is introduced between melting and annealing steps. This way, the opposite strands of abundant amplicons would mostly reanneal and not amplify in subsequent cycles; the rate of reannealing is proportional to square of their concentration. The temperature for this intermediate step is much higher than the Tm for primers, but lower than the Tm for the amplicons; typically this $C_0t$ temperature is between 70° C. and 85° C. During the $C_0t$ step, the less abundant amplicons do not reanneal much and continue amplification. Essentially we are lowering the PCR plateau for the abundant amplicons that are mostly melting and reannealing at late cycles and not consume the PCR reagents, so that slower amplicons have more PCR cycles to catch up. The total number of PCR cycles can also be increased to 40-55.

In a typical experiment DNA from each sample is mixed with universal primers containing sample barcodes, pooled blocked primers and the PCR mix. After PCR all wells are pooled together and cleanup is usually performed, e.g., using SPRI (solid phase reversible immobilized) beads. The key advantage of this "closed tube" protocol is that wells are opened after sample bar codes (indexes) were attached to the amplicons eliminating the risk of carry over contamination between samples. In addition to minimize a chance of carry over contamination between different experiments one can employ a regular dUTP/UDG (uracil DNA glycosylase) method (Longo et. al. *Gene*, 93 pp 125-8, 1990). Finally, we would like to note here that it is possible to run 2 cycles of PCR first and then, after an optional clean-up, add universal sample bar-coded primers to the reaction and continue PCR.

The chance of carry over contamination after two cycles is low, but this workflow is less convenient than the closed tube approach we describe above.

Previously, investigators (Bi and Stambrook, "Detection of known mutation by proof-reading PCR", *Nucleic Acids Research*, 1998, 26, pp 3073-3075 and Lin-Ling et al. "Single-base discrimination mediated by proofreading inert allele specific primers", *J Biochem Mol Biol.* 2005, 38, pp 24-7) used primers with a mismatch at the 3'-end (it can also be up to 6 bases away) in PCR with exo+ polymerases. Blocked primers with intentional mismatches at or near the 3' end can also be used for the NGS enrichment, e.g., when using 3'-NH2 or 3'-dideoxy base. This "intentional mismatch" method would be useful to amplify several mutations in the same position or same codon or in some cases even adjacent codons using a single wild-type (normal) primers: predominantly mutated molecules that have a mismatch will amplify.

Commercially-available thermostable DNA polymerases generally have either 5' or 3' exonuclease activities, but not both. Therefore, to use DNA detection using 5'-nuclease (TaqMan, or methods described in U.S. patent application Ser. No. 12/931,803) and 3'-blocked primers one can use a mixture of polymerase with 5'-exonuclease activity and either a separate enzyme with the 3'-exonuclease activity or a polymerase with 3'exonuclease activity. Mixtures of 3'-exo+ and Taq polymerase (5'-exo+ and 3'-exo−) are often used for long range PCR: most of extensions are performed by the more processive Taq, but if it incorporates a mismatch and dissociates from the template the 3'-exo+ enzyme can correct the mismatch. Thus 3'-blocked primers can be employed to generate 5'-nuclease signal in qPCR using a mixture of 3'-exo+ and 5'-exo+ polymerases.

Figure 9A:
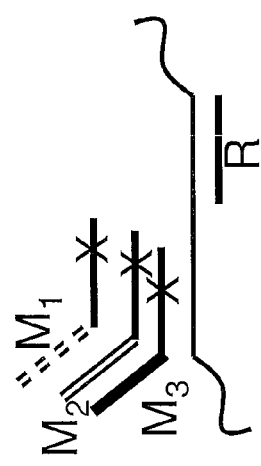
FIG. 9. Schema for increasing sensitivity of detection for mutation-specific primers targeting closely spaced mutations using different 5'-tags. "R" and "X" are examples of an RNA base in locus and mutation-specific primers, respectively. (A) Three allele (mutation) specific primers targeting three closely-spaced mutations, shown as "X" have different $M_1$, $M_2$ and $M_3$ tags. (B) Encoding allele-specific primers (as in A) with universal Ai tag and locus-specific primer with Bi and Ci tags used for detection reaction. (C) Example of temperature cycling program.

In many genes several mutations in the same or adjacent codons result in a similar phenotype. Examples include multiple activating somatic mutations in cancer in KRAS codons 12 and 13: 12ALA, 12ASP, 12ARG, 12CYS, 12SER, 12VAL and 13ASP. Activating somatic mutations in BRAF gene codon 600: V600E and V600K is another example. Similarly, many drug resistance mutation in bacteria and viruses occur in the same or nearby codons, e.g., HIV becomes resistant to neverapine (NVP) if any one of these amino acid changes in codons 188 or 190 has occurred: Y188[LHC] or G190[ASE]. *Mycobacterium tuberculosis* (MTB) becomes resistant to rifampicin, if codon 526 in rpoB gene is mutated to encode one of 5 amino acids: H526 [LRYDN]. When using multiplexed mutation-specific PCR and detecting all nearby mutations, the target-specific primers share similar sequences; they "overlap" in the target region they anneal to. This may cause a loss of sensitivity as these primers are competing with each other. For example, if six mutation-specific primers target mutations in the same codon only one primer is a perfect match for a given mutation, but other five primers have a small thermodynamic disadvantage: they have only one or two mismatches when binding to the same mutated target region. FIG. 9 shows an example of three primers that target three closely spaced mutations, shown as "X": they anneal to the shared region in the target DNA. The loss of sensitivity should be less than 3× in the first cycle and it is, generally, not detrimental to PCR, as less than 2 ($2^2$=4) additional cycles will be required to overcome a 3× loss in sensitivity. But if this competition between primers continues to the end of PCR, the loss of sensitivity would be substantial. The 5' $M_{1-3}$-tags in FIG. 9a help to minimize primer competition starting cycle 3. At cycle 1 one of the M-tags that matches the mutation is incorporated into the amplicon. At cycle 2 this M-tag is copied. Starting cycle 3 the mutation-specific primer that has extended at cycle 1 has a significant thermodynamic advantage over the competing primers: it forms dsDNA over 100% of its length, including the M-tag; the competing primers have a mismatched M-tags and much lower Tm. One can increase the annealing temperature starting cycle 3 or use high annealing temperature (relative to the predicted Tm of allele-specific parts of the primers) starting from cycle 1.

In case of allele-specific PCR with mutation-specific and universal primers, after the first two cycles that incorporate universal tags, the universal primers continue amplification to generate signal with little competition from low concentration target-specific primers. But in some cases, e.g., rhPCR, the specificity of mutation detection increases exponentially, if target-specific rhPCR primers, rather than the universal ones continue amplification beyond the first two cycles. To achieve this, we propose using additional 5'-tags in mutation-specific primers, tags $M_{1-3}$ in FIG. 9. Each mutation-specific primer will be incorporates a different M tag in the first cycle and complements or this tag at the 2nd cycle. We then use a high annealing temperature, e.g., 68-74° C. (FIG. 9c shows an example), so that the matching mutation-specific primers that were extended in the first two cycles anneal and hybridize with their 5'-tag and thus have a significant thermodynamic advantage over mismatched mutation-specific primers. At high annealing temperature the matching mutation-specific primers that "won" the competition during the first cycle gains an advantage over competing mutation-specific primers that have mismatched universal tags. Thus, we prevent the exponential loss of sensitivity, but preserve the exponential gain in specificity for mutation-specific rhPCR.

Figure 9B:
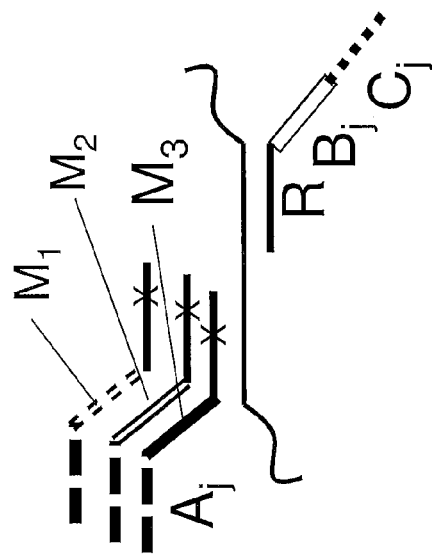
Figure 9C:
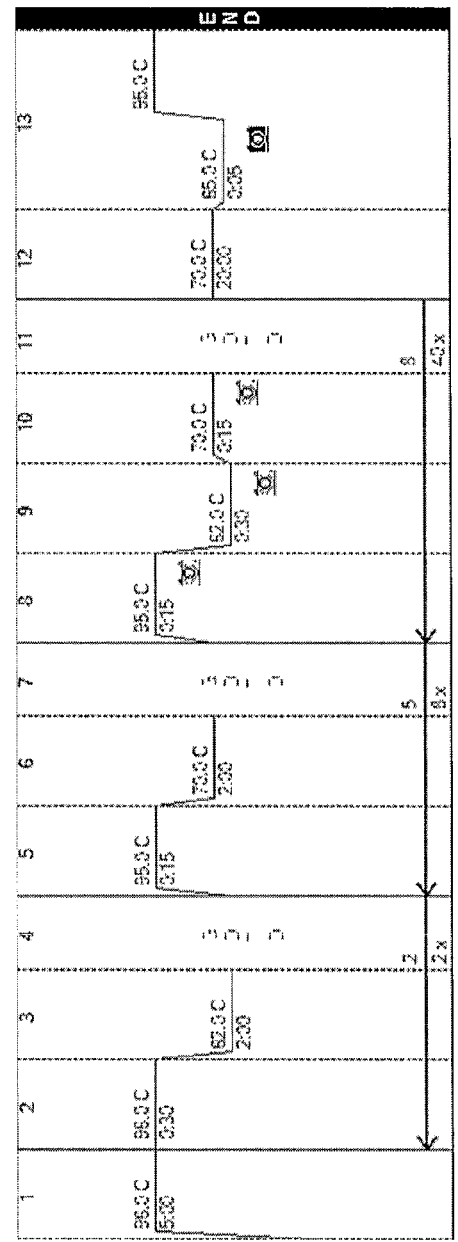

FIG. 9b shows how this method can be combined with encoding detection reaction, described above. In this case mutation-specific $M_{1-3}$ tags become middle tags between the target-specific 3'-regions and universal 5'-tags. The high annealing temperature after cycle two, also helps to prevent priming by universal primers in early cycling that we described above, exponentially increasing specificity of rhPCR or exonuclease-dependent PCR with mutated base downstream from the cleavage site. FIG. 9c shows cycling protocol used: 2 cycles with 62° C. annealing, followed by 8 cycles with 70° C. annealing, both using long 2 minutes anneal-extend time and followed by fast 40 cycles with 30 sec @62° C. and 15 sec @70° C.

Figure 10A:
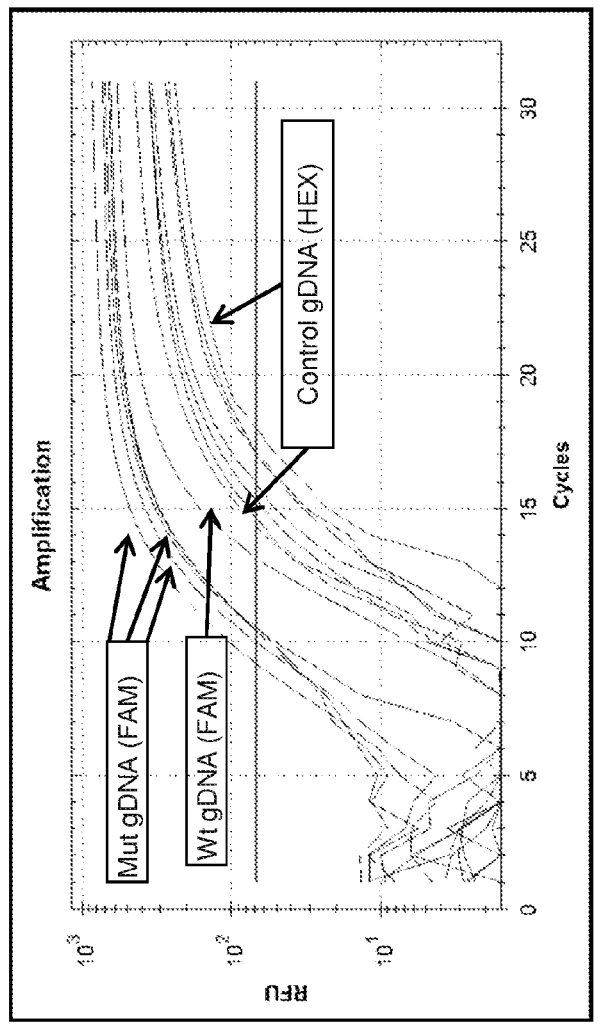
FIG. 10. rhPCR using RNase H blocked primers for MTB (tuberculosis) drug resistance mutations for rifampicin (RIF) in codon 526 (aka 445). Any one of six mutation in the codon #526 of rpoB gene generate FAM signal, HEX signal is control. (A) amplification curves; (B) cycling program.
Figure 10B:
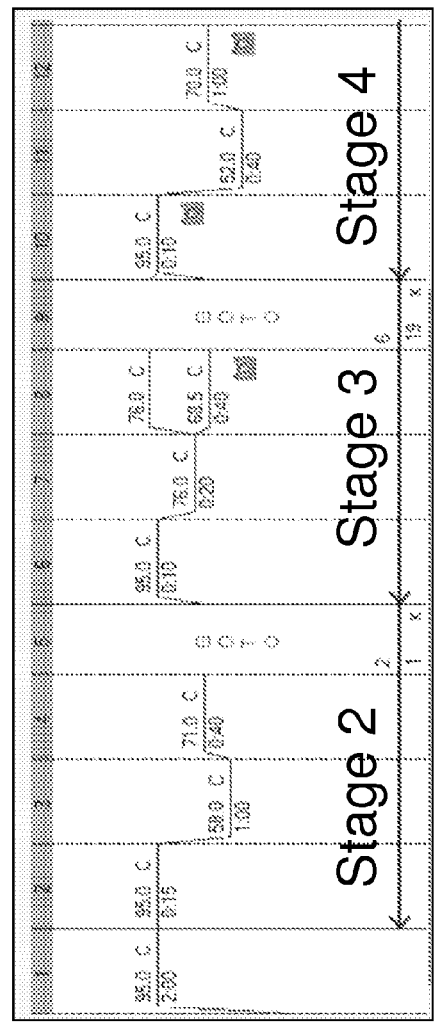

FIG. 10 shows multiplex rhPCR/qPCR detection of six mutations in codon 526 (445) of *Mycobacterium tuberculosis* (MTB) rpoB gene that cause resistance to rifampicin (RIF). Closed tube multiplex PCR contained: (a) six mutation-specific primers (Table 2), (b) a single shared reverse primer; (c) a separate primer pair for control MTB region with different universal tags (so that this control region is detected by HEX signal); (d) two labeled primers with FAM/HEX dye and quencher (see oligo #5 in Table 1 as an example) and (e) a regular primer as shown in FIG. 4c (dashed line), see US patent application Ser. No. 12/931, 803. Blocked mutation specific primers with additional competition tags and Ct values for mutated and wild-type MTB are shown in Table 2. The mutation-specific primers contain several functional parts from 5' to 3': same universal tags to generate the same dye signal, different for each mutation-specific primer non-template "competition" tags (underlined), MTB-specific region: DNA, an RNA base ("rN" in italics) and C3-blocked 3'-end that has either 3' C3 or two internal C3 spacers (underlined).

TABLE 2

Use of blocked primers with "completion" tags for mutation detection.

| Mutation | Primer Sequences | FAM | HEX | ΔCt |
|---|---|---|---|---|
| H526D-445gAC | CAAGCTGATCCGTACAACGCTGAC GTCCCGCTGTCGGGGTTGACCrGA/iSpC3//iSpC3/A (SEQ ID NO: 8) | 10.24 | 14.44 | 4.2 |
| H526Y-445tAC | CAAGCTGATCCGTACAGTCGTGCA CACGCTGTCGGGGTTGACCrUACAA/3SpC3/ (SEQ ID NO: 9) | 9.78 | 16.13 | 6.35 |
| H526L-445CtC | CAAGCTGATCCGTACAGAGGACCA TGCTGTCGGGGTTGACCCrUCAAG/3SpC3/ (SEQ ID NO: 10) | 9.01 | 17.01 | 8 |
| H526N-445aAC | CAAGCTGATCCGTACAGAGCTGtA GTCCGCTGTCGGGGTTGACCrAA/iSpC3//iSpC3/A (SEQ ID NO: 11) | 10.17 | 16.25 | 6.08 |
| H526S-445agC | CAAGCTGATCCGTACATCCAATAA CGTGTCGGGGTTGACCrAGCAAA/3SpC3/ (SEQ ID NO: 12) | 12.98 | 14.97 | 1.99 |
| H526R-445CgC | CAAGCTGATCCGTACAACCACAGT GTCGCTGTCGGGGTTGACCCrGC/iSpC3//iSpC3/G (SEQ ID NO: 13) | 10.31 | 13.78 | 3.48 |
| MTB-WT gDNA |  | 12.94 | 13.6 | 0.66 |

The qPCR cycling (FIG. 9b) has four stages:
1. Denaturation: 95° C., 2:00 Min
2. Stage 2: 2 cycles: (95° C., 15 sec, 58° C. 1:00 Min, 71° C. 40 sec
3. Stage 3: 20 cycles: (95° C., 10 sec, 76° C., 20 sec, 74° C., 40 sec)
4. Stage 4: 30 cycles: (95° C., 10 sec+Plate Read, 52° C., 40 sec, 70° C., 1:00 Min+Plate Read)

During the first 2 cycles there is competition between the six primers: if a primer that does not match the mutation in the template anneals, it may stay annealed long enough and not let the matching primer to anneal, causing a loss of sensitivity. At cycle 2 the 5' "competition" tag on the primer than extended at cycle 1 is copied. At stage 3, starting cycle 3, we use a high annealing temperature, so that the matching primer that extended at cycle 1 has a perfectly matching competition tag and much higher Tm than the five primers specific for the other five mutations. Also at high annealing temperatures, the PCR is driven by long rhPCR primers (FIG. 1a), rather than the short universal primer in FIG. 1c. At stage 4, at a lower annealing temperature, the annealing of the universal primers present at high concentrations is favored and fluorescent signal is being generated.

The method and compositions described above can be used for highly multiplexed PCR followed by sequencing (NGS), array hybridization, electro-chemical surface detection or electrophoresis (CE). In case of NGS, one can envision multiplexing a large number of blocked target-specific primers with two universal primers that have sequencing tags, e.g., so called P5 and P7 in case of Illumina and optional bar-codes that are used to identify different samples. This would be a simple sample prep protocol that does not require complex additional ligation and other steps that require opening tubes after PCR and risk carry over contamination. Multiplex PCR inevitably generates a lot of primer dimers, but blocked primers diminish this side reaction. Additionally, the $C_0t$ method described above can be used at late cycles to normalize the amount of different amplicons in multiplex PCR.

DEFINITIONS

As used herein, "Target nucleic acids" or "target" are DNA/RNA molecules present in a sample prior to any changes in the nucleic acid sequence composition during sample processing. A certain location target DNA/RNA is called locus.

As used herein, a "primer" or "unblocked primer" is an oligo with its 3' termini extendable by a polymerase after it anneals to the template. In some embodiments, primers can have one or several labels.

As used herein, a "3'-blocked (blocked) primer" cannot be extended by a polymerase: a 3'-OH is missing or a chemical moiety is used to block polymerase extension. For example, primer may have 3'-phosphate, C3 spacer (3' Propyl), Spacer 9/18 either at the 3' end or close to it (see Table 2 for examples), 1',2'-Dideoxyribose (dSpacer), 3' Hexanediol, 2'-3'-Dideoxy, 3'-deoxy bases, inverted dT (see modified bases and spacers by IDT), 3'-amine or any other moiety that disables polymerase extension, see for example Table 2 in Lin-Ling et al. Single-base discrimination mediated by proofreading inert allele specific primers. Lin-Ling et al., *J Biochem Mol Biol.* 2005 Jan. 31; 38(1):24-7

As used herein, a "mutation (allele) specific primer" has the 3'-end specific for the target mutations, rather the normal (wild type) bases and optionally additional intentional mismatches of modified bases near the 3'-end.

As used herein, a "probe" is an oligo that carries at least one label that is used to generate a detectable signal. Probes have a blocked 3' end to prevent their extension by a polymerase.

As used herein, "qPCR" is quantitative Polymerase Chain Reaction, where signal is measured during and/or at the end of PCR.

As used herein, a "universal tag" is a part of the primer or amplicon with an artificial sequence that does not match the target nucleic acid, with exception of very short tags that either intentionally or accidentally match target nucleic acid.

As used herein, a "universal primer/probe" is a primer and/or probe that comprises one or more universal tags that do not match the target nucleic acid and by chance or intentionally may comprise a very short stretch of target nucleic acid that occurs at the locus that is detected.

As used herein, "encoding or linking reaction" is a step within the target nucleic acid detection that generates "encoded DNA molecules with universal tags". PCR pre-amplification with 5' tailed (tagged) primers is an example of an encoding or linking reaction.

As used herein, a "template" is a nucleic acid to which primers, probes, or amplicons anneal; the sequence of the template can be either target or complementary to universal tags.

As used herein, "first PCR cycles" are 1, 2 or more cycles when polymerase extends target-specific primers.

As used herein, a "closed tube PCR or reaction" is a reaction that generates signal or incorporates sample bar-codes for NGS without the need to open a well/tube after PCR, thus eliminating possibility of carry over contamination in an experiment that processes several samples in parallel.

As used herein, "cleavage or unblocking" is an enzymatic step that modifies a blocked primer opening up a 3'-OH group that can be extended by polymerase after this blocked primer forms a double-stranded DNA annealing to the template. Different enzymes can be used for the unblocking: Endonuclease IV (EndoIV), Human apurinic/apyrimidinic (AP) endonuclease, APE 1, other 3'-exonucleases, and DNA polymerases with 3'-exonuclease (exo+) activity. RNase H cleaves RNA bases and several DNA repair enzymes can cleave at a modified base leaving an extendable 3'-OH.

Target Nucleic Acid Sources and Molecular Biology Reagents and Techniques

As will be appreciated, target nucleic acids that find use in the invention can be obtained from a wide variety of sources. For example, target nucleic acids can be obtained from biological or laboratory samples including cells, tissues, lysates, and the like. In certain aspects, the source of target nucleic acids includes cells or tissues from an individual with a disease, e.g., cancer or any other disease of particular interest to the user.

A plethora of kits are commercially available for the purification of target nucleic acids from cells or tissues, if desired (see, e.g., EASYPREP™, FLEXIPREP™, both from Pharmacia Biotech; STRATACLEAN™ from Stratagene; QIAPREP™ from Qiagen). In addition, essentially any target nucleic acid can be custom or standard ordered from any of a variety of commercial sources.

General texts which describe molecular biological techniques for the isolation and manipulation of nucleic acids include Berger and Kimmel, Guide to Molecular Cloning Techniques, Methods in Enzymology volume 152 Academic Press, Inc., San Diego, Calif. (Berger); Sambrook et al., Molecular Cloning: A Laboratory Manual (3rd Ed.), Vol. 1-3, Cold Spring Harbor Laboratory, Cold Spring Harbor, N.Y., 2001 ("Sambrook") and Current Protocols in Molecular Biology, F. M. Ausubel et al., eds., Current Protocols, a joint venture between Greene Publishing Associates, Inc. and John Wiley & Sons, Inc., (supplemented through the current date) ("Ausubel")).

Labeling strategies for labeling nucleic acids and corresponding detection strategies can be found, e.g., in Haugland (1996) Handbook of Fluorescent Probes and Research Chemicals Sixth Edition by Molecular Probes, Inc. (Eugene Oreg.); or Haugland (2001) Handbook of Fluorescent Probes and Research Chemicals Eighth Edition by Molecular Probes, Inc. (Eugene Oreg.) (Available on CD ROM).

A number of embodiments of the present invention utilize the principles of polymerase chain reaction (PCR). PCR methods and reagents, as well as optimization of PCR reaction conditions (e.g., annealing temperatures, extension times, buffer components, metal cofactor concentrations, etc.) are well known in the art. Details regarding PCR and its uses are described, e.g., in Van Pelt-Verkuil et al. (2010) Principles and Technical Aspects of PCR Amplification Springer; 1 st Edition ISBN-10: 9048175798, ISBN-13: 978-9048175796; Bustin (Ed) (2009) The PCR Revolution: Basic Technologies and Applications Cambridge University Press; 1 st edition ISBN-10: 0521882311, ISBN-13: 978-0521882316; PCR Protocols: A Guide to Methods and Applications (Innis et al. eds) Academic Press Inc. San Diego, Calif. (1990) (Innis); Chen et al. (ed) PCR Cloning Protocols, Second Edition (Methods in Molecular Biology, Volume 192) Humana Press; and in Viljoen et al. (2005) Molecular Diagnostic PCR Handbook Springer, ISBN 1402034032.

As noted herein, the universal detection steps of the present invention can be performed in real-time, e.g., where one or more detectable signals (if any) corresponding to the presence or amount of one or more target nucleic acids are detected at the conclusion of one or more PCR cycles prior to completion of thermal cycling. Real-time/quantitative PCR techniques are known in the art. Detailed guidance can be found in, e.g., Clementi M. et al (1993) PCR Methods Appl, 2:191-196; Freeman W. M. et al (1999) Biotechniques, 26:112-122, 124-125; Lutfalla G. and Uze G. (2006) Methods Enzymol, 410: 386-400; Diviacco S. et al (1992) Gene, 122: 313-320 Gu Z. et al (2003)/. Clin. Microbiol, 41: 4636-4641. Real-time (e.g., quantitative) PCR detection chemistries are also known and have been reviewed in, e.g. Mackay J., Landt O. (2007) Methods Mol. Biol, 353: 237-262; Didenko V. V. (2001) BioTechniques, 31, 1106-1121; and Mackay L M. et al (2002) Nucleic Acids Res., 30: 1292-1305, which are incorporated herein by reference in their entireties for all purposes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A PCR reaction mixture comprising:
   (a) at least one pair of target-specific primers comprising universal 5' tags, where at least one target-specific primer cannot be extended by polymerase (3'-blocked primer);
   (b) at least one pair of universal primers adapted to prime on a complement of the universal 5' tags, and at least one of the universal primers comprises a bar-code identifying a sample;
   (c) an enzyme that unblocks the 3'-blocked primer after it anneals to the DNA target generating a 3'-OH end; and
   (d) a polymerase that extends unblocked primers during one or more initial PCR cycles; and subsequently extends universal primers driving amplification in a closed tube reaction.

2. The PCR reaction mixture of claim 1, wherein multiple blocked target-specific primers amplify multiple targets (multiplex PCR) and target-specific primers for targets that are to be detected together comprise the same universal tags.

3. The PCR reaction mixture of claim 1, wherein the concentration of the target-specific primers is at least 40-fold less than the concentration of the universal primers.

4. The reaction mixture of claim 2, wherein universal primers are labeled and different universal primers are adapted to detect targets by priming on the universal tag complements of the amplicons generated by the blocked primers.

5. A method to detect or enrich target nucleic acids in one or more samples in a closed tube reaction, comprising:
   carrying out a PCR amplification reaction with one or more 5' tagged target-specific primer(s) comprising a blocked 3'-end and a 5' universal tag, and
   providing in the amplification reaction one or more universal primers adapted to prime on a complement of one or more of the universal tags; wherein at least one of the universal primers comprises a sample bar-code;
   such that during initial PCR cycles, the target-specific primers anneal, get unblocked and extend on target DNA; and in subsequent PCR cycles, the universal primers drive PCR amplification in the closed tube reaction.

6. The method of claim 5, wherein a read-out for the detection of nucleic acids is selected from the group consisting of: real-time or end-point PCR for sequencing, NGS enrichment, fragment sizing using electrophoresis, surface hybridization, amplicon melting, molecular weight determination via electrophoresis, and mass spectrometry.

7. The reaction mixture of claim 1 or the method of claim 5, wherein the one or more 3' blocked primer(s) comprise(s) a C3 spacer(s) or another 3'-blocking modification.

8. The reaction mixture or method of claim 7, comprising, or comprising the use of, a DNA polymerase with 3'-exonuclease activity or an endonuclease to unblock the primers.

9. The reaction mixture or method of claim 7, comprising, or comprising the use of, a blocked primer comprising an abasic site to anneal to the target on both sides of the abasic site, and an endonuclease IV to cleave 5' from the abasic site, unblocking the primer.

10. The reaction mixture of claim 1 or the method of claim 5, wherein the primer comprises at least one RNA base, and further comprising, or comprising the use of, RNase H enzyme for unblocking the primer.

11. The reaction mixture of claim 2 or the method of claim 5 used for PCR enrichment for sequencing, wherein the blocked target-specific primers comprise random molecular barcodes between a 3' target specific region and the 5' universal tag, allowing identification of individual DNA strands amplified in PCR, such that the first two PCR cycles incorporate random molecular bar-codes for each target DNA strand present in the sample.

12. The method of claim 5, wherein the PCR reaction is normalized by slowing down cooling from melting to annealing temperature during late PCR cycles, such that the majority of abundant target amplicons reanneal and do not amplify, but rare ones continue their amplification.

13. The reaction mixture of claim 1, wherein the blocked target-specific primers separately comprise different universal tags.

14. The reaction mixture of claim 1, wherein the enzyme that unblocks the 3'-blocked primer is a polymerase with 3'-exonuclease activity.

15. The method of claim 5, wherein the blocked target-specific primers separately comprise different universal tags.

16. The method of claim 5, further comprising pooling PCR amplifications of two or more samples and determining sequences of amplicons in the pooled amplifications optionally including all the bar-codes used in both target-specific and universal primers.

17. The method of claim 16, further comprising assigning an amplicon sequence to a particular sample based on the sample bar code.

18. The method of claim 5, further comprising shifting primer annealing conditions to a lower annealing temperature or to a shorter annealing time after completion of two PCR amplification cycles thereby favoring annealing of the universal primers.

19. The method of claim 5, wherein the universal primers comprise blocked 3' ends.

20. The method of claim 5, further comprising next generation sequencing (NGS) of an amplicon product of the closed tube reaction.

* * * * *